(«12») United States Patent
Kadoma et al.

(10) Patent No.: US 9,105,852 B2
(45) Date of Patent: Aug. 11, 2015

(54) BIPYRIDINE COMPOUND, LIGHT-EMITTING ELEMENT MATERIAL, ORGANIC SEMICONDUCTOR MATERIAL, LIGHT-EMITTING ELEMENT, DISPLAY MODULE, LIGHTING MODULE, LIGHT-EMITTING DEVICE, LIGHTING DEVICE, DISPLAY DEVICE AND ELECTRONIC DEVICE

(71) Applicant: Seminconductor Energy Laboratory Co., Ltd., Kanagawa-ken (JP)

(72) Inventors: Hiroshi Kadoma, Kanagawa (JP); Takahiro Ushikubo, Tochigi (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 352 days.

(21) Appl. No.: 13/767,007

(22) Filed: Feb. 14, 2013

(65) Prior Publication Data

US 2013/0214260 A1  Aug. 22, 2013

(30) Foreign Application Priority Data

Feb. 17, 2012  (JP) .................................. 2012-032720

(51) Int. Cl.
*H01L 51/00* (2006.01)
*C07D 213/22* (2006.01)
*H01L 51/50* (2006.01)

(52) U.S. Cl.
CPC .......... *H01L 51/0067* (2013.01); *C07D 213/22* (2013.01); *H01L 51/0058* (2013.01); *H01L 51/0072* (2013.01); *H01L 51/5072* (2013.01); *H01L 2251/308* (2013.01)

(58) Field of Classification Search
None
See application file for complete search history.

(56) References Cited

U.S. PATENT DOCUMENTS 6,603,007 B1  8/2003  Shintou
7,221,095 B2  5/2007  Yamazaki et al.
(Continued)

FOREIGN PATENT DOCUMENTS

EP   1 231 207 A1   8/2002
JP   2001-97950    4/2001
(Continued)

OTHER PUBLICATIONS

Kendurkar, P.S. et al, "Reactions of N-pyridinium Phenacylides with α,β-unsaturated Keytones, I. Synthesis of 2,4,6-triaryl-substituted Pyridines," Zeitschrift fuer Naturforschung, Teil B: Anorganische Chemie, Orgar Chemie, Biochemie, Biophysik, Biologie, vol. 29 (7/8), 1974, pp. 552-555 (Abstract —one page).

(Continued)

*Primary Examiner* — Robert S Loewe
(74) *Attorney, Agent, or Firm* — Husch Blackwell LLP

(57) ABSTRACT

A light-emitting element having good characteristics can be obtained by using a bipyridine compound having at least one 2,2'-bipyridine structure and at least two anthracene skeletons as light-emitting element materials. In particular, a bipyridine compound in which an anthracene skeleton is bonded to each of the 5-position and the 6-position of 2,2'-bipyridine through an arylene group can be synthesized and a light-emitting element having good characteristics can be obtained in the case where the bipyridine compound is used as a light-emitting element material.

22 Claims, 17 Drawing Sheets

(56) References Cited

U.S. PATENT DOCUMENTS

| | | | |
|---|---|---|---|
| 7,224,118 B2 | 5/2007 | Yamazaki et al. | |
| 7,411,344 B2 | 8/2008 | Yamazaki et al. | |
| 7,420,203 B2 | 9/2008 | Tsutsui et al. | |
| 7,473,923 B2 | 1/2009 | Tsutsui et al. | |
| 7,514,159 B2 | 4/2009 | Nakamura | |
| 7,867,629 B2 | 1/2011 | Yamamoto et al. | |
| 8,142,911 B2 | 3/2012 | Kadoma et al. | |
| 2003/0045642 A1* | 3/2003 | Wu et al. | 525/204 |
| 2008/0093981 A1 | 4/2008 | Nakamura et al. | |
| 2009/0134780 A1* | 5/2009 | Ono et al. | 313/504 |
| 2009/0256473 A1* | 10/2009 | Kim et al. | 313/504 |
| 2010/0327265 A1* | 12/2010 | Kimura et al. | 257/40 |
| 2012/0178933 A1 | 7/2012 | Kadoma et al. | |

FOREIGN PATENT DOCUMENTS

| | | |
|---|---|---|
| JP | 2004-2297 | 1/2004 |
| JP | 2009-298778 | 12/2009 |
| WO | WO 01/19815 A1 | 3/2001 |

OTHER PUBLICATIONS

Yu, S.C. et al, "Synthesis and Characterization of Poly(benzobisoxazole)s and Poly(benzobisthiazole)s with 2,2'-Bipyridyl Units in the Backbone," Macromolecules, vol. 31, 1998, pp. 5639-5646.

Goldsmith, C.R. et al., "C—H Bond Activation by a Ferric Methoxide Complex: Modeling the Rate-Determining Step in the Mechanism of Lipoxygenase," Journal of the American Chemical Society, vol. 124, No. 1, 2002, pp. 83-96.

Ohnishi, T. et al, "A Method of Measuring an Energy Level," High Molecular EL Materials Development of Light-Emitting High Molecular Compounds, Kyoritsu Shuppan, Dec. 25, 2004, p. 64-67 (with English translation, pp. 1-3).

Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID Digest 04: SID International Symposium Digest of Technical Papers, vol. 35, 2004, pp. 900-903.

* cited by examiner

BIPYRIDINE COMPOUND, LIGHT-EMITTING ELEMENT MATERIAL, ORGANIC SEMICONDUCTOR MATERIAL, LIGHT-EMITTING ELEMENT, DISPLAY MODULE, LIGHTING MODULE, LIGHT-EMITTING DEVICE, LIGHTING DEVICE, DISPLAY DEVICE AND ELECTRONIC DEVICE

BACKGROUND OF THE INVENTION

1. Field of the Invention

The present invention relates to a bipyridine compound that can be used for a light-emitting element material. The present invention also relates to a light-emitting element material and an organic semiconductor material each using the bipyridine compound. The present invention further relates to a light-emitting element, a light-emitting module, a light-emitting device, a lighting device, a display device, and an electronic device each using the bipyridine compound.

2. Description of the Related Art

As next generation lighting devices or display devices, display devices using light-emitting elements (organic EL elements) in which organic compounds are used as light-emitting substances have been developed rapidly because of their advantages of thinness, lightweightness, high-speed response to input signals, low power consumption, and the like.

In an organic EL element, voltage application between electrodes between which a light-emitting layer is provided causes recombination of electrons and holes injected from the electrodes, which brings a light-emitting substance into an excited state, and the return from the excited state to the ground state is accompanied by light emission. Since the wavelength of light emitted from a light-emitting substance is peculiar to the light-emitting substance, use of different types of organic compounds for light-emitting substances makes it possible to provide light-emitting elements which exhibit various wavelengths, i.e., various colors.

In the case of display devices which are expected to display images, such as displays, at least three-color light, i.e., red light, green light, and blue light are necessary for reproduction of full-color images. Furthermore, in application to lighting devices, light having wavelength components evenly spreading in the visible light region is ideal for obtaining a high color rendering property, but actually, light obtained by mixing two or more kinds of light having different wavelengths is often used for lighting application. Note that it is known that mixing light of three colors of red, green, and blue allows generation of white light having a high color rendering property.

Light emitted from a light-emitting substance is peculiar to the substance as described above. However, important performances as a light-emitting element, such as lifetime, power consumption, and even emission efficiency, are not only dependent on the light-emitting substance but also greatly dependent on layers other than the light-emitting layer, an element structure, properties of an emission center substance and a host material, compatibility between them, carrier balance, and the like. Therefore, there is no doubt that many kinds of light-emitting element materials are necessary for a growth in this field. For the above-described reasons, light-emitting element materials with a variety of molecular structures have been proposed (e.g., see Patent Document 1).

As a substance of a host material in a host-guest type light-emitting layer or a substance contained in each transport layer in contact with a light-emitting layer, a substance having a wider band gap or a higher triplet level (a larger energy difference between a triplet excited state and a singlet ground state) than an emission center substance is used for efficient conversion of excitation energy into light emission from the emission center substance.

Therefore, a host material and a carrier-transport material each having a further wider band gap are necessary in order that light emission having a shorter wavelength such as blue fluorescence is efficiently obtained. It is difficult to develop a substance to be a light-emitting element material which has a wide band gap while enabling a balance between important characteristics of a light-emitting element, such as low driving voltage and high emission efficiency.

REFERENCE

Patent Document

[Patent Document 1] Japanese Published Patent Application No. 2004-002297

SUMMARY OF THE INVENTION

In view of the above, an object of one embodiment of the present invention is to provide a bipyridine compound which can be used for a transport layer or as a host material or a light-emitting material of a light-emitting element. Specifically, an object of one embodiment of the present invention is to provide a bipyridine compound which makes it possible to obtain a light-emitting element having good characteristics even when used in a light-emitting element emitting light with a short wavelength such as blue fluorescence.

Another object of one embodiment of the present invention is to provide a light-emitting element material using the bipyridine compound.

Another object of one embodiment of the present invention is to provide a light-emitting element using the bipyridine compound.

Another object of one embodiment of the present invention is to provide a display module, a lighting module, a light-emitting device, a lighting device, a display device, and an electronic device each using the bipyridine compound.

It is only necessary that at least one of the above-described objects be achieved in the present invention.

The present inventors have found that a light-emitting element having good characteristics can be obtained by using a bipyridine compound having at least one 2,2'-bipyridine structure and at least two anthracene skeletons as light-emitting element materials. In particular, the present inventors have found that a bipyridine compound in which an anthracene skeleton is bonded to each of the 5-position and the 6-position of 2,2'-bipyridine through an arylene group can be synthesized and a light-emitting element having good characteristics can be obtained in the case where the bipyridine compound is used as a light-emitting element material.

Specifically, one embodiment of the present invention is a bipyridine compound represented by General Formula (G1).

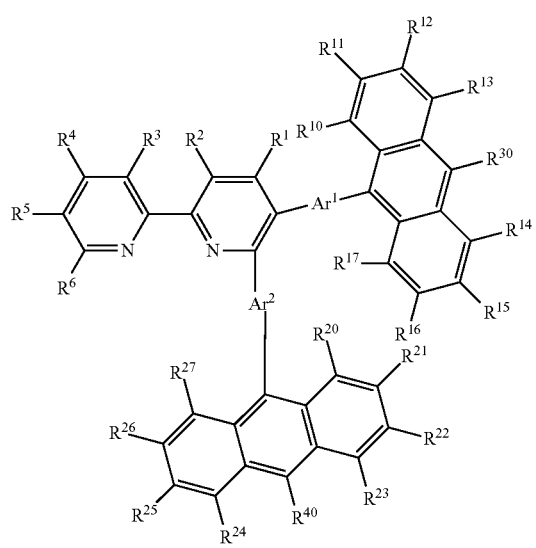

(G1)

Note that in the formula, $R^1$ to $R^6$, $R^{10}$ to $R^{17}$, and $R^{20}$ to $R^{27}$ each independently represent hydrogen or an alkyl group having 1 to 4 carbon atoms; $Ar^1$ and $Ar^2$ each independently represent an arylene group having 6 to 13 carbon atoms; and $R^{30}$ and $R^{40}$ each independently represent any of hydrogen, an alkyl group having 1 to 4 carbon atoms, and an aryl group having 6 to 13 carbon atoms.

In the bipyridine compound represented by General Formula (G1), a structure in which all of $R^1$ to $R^6$ are hydrogen is preferable in terms of cost. That is, another embodiment of the present invention is a bipyridine compound represented by General Formula (G2).

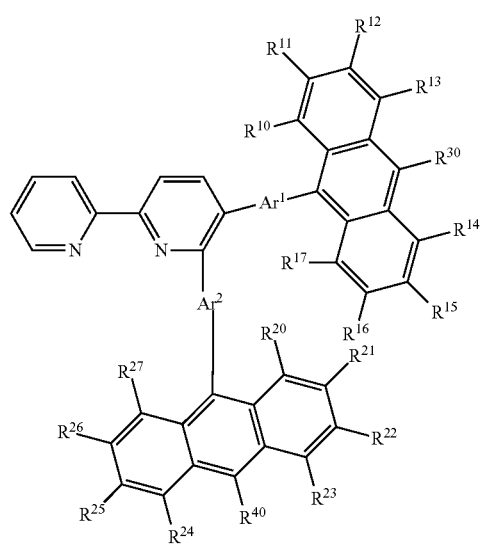

(G2)

Note that in the formula, $R^{10}$ to $R^{17}$ and $R^{20}$ to $R^{27}$ each independently represent hydrogen or an alkyl group having 1 to 4 carbon atoms; $Ar^1$ and $Ar^2$ each independently represent an arylene group having 6 to 13 carbon atoms; $R^{30}$ and $R^{40}$ each independently represent any of hydrogen, an alkyl group having 1 to 4 carbon atoms, and an aryl group having 6 to 13 carbon atoms.

For the same reason as the above, it is more preferable that all of $R^{10}$ to $R^{17}$ and $R^{20}$ to $R^{27}$ be hydrogen in the bipyridine compound represented by General Formula (G2). That is, another embodiment of the present invention is a bipyridine compound represented by General Formula (G3).

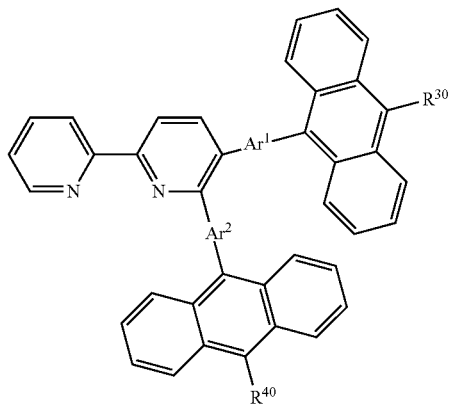

(G3)

Note that in the formula, $Ar^1$ and $Ar^2$ each independently represent an arylene group having 6 to 13 carbon atoms; and $R^{30}$ and $R^{40}$ each independently represent any of hydrogen, an alkyl group having 1 to 4 carbon atoms, and an aryl group having 6 to 13 carbon atoms.

Another embodiment of the present invention is a bipyridine compound in which $R^{30}$ and $R^{40}$ in the above formula each independently represent an aryl group having 6 to 13 carbon atoms.

Another embodiment of the present invention is a bipyridine compound in which $R^{30}$ and $R^{40}$ in the above formula each independently represent a phenyl group or a biphenyl group.

Another embodiment of the present invention is a bipyridine compound in which $Ar^1$ and $Ar^2$ in the above formula each independently represent a phenylene group or a biphenyldiyl group.

Another embodiment of the present invention is a bipyridine compound represented by Structural Formula (100).

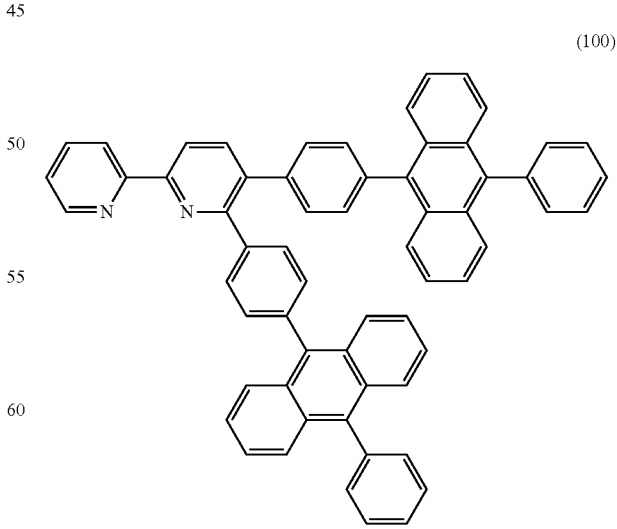

(100)

Another embodiment of the present invention is a bipyridine compound represented by Structural Formula (106).

(106)

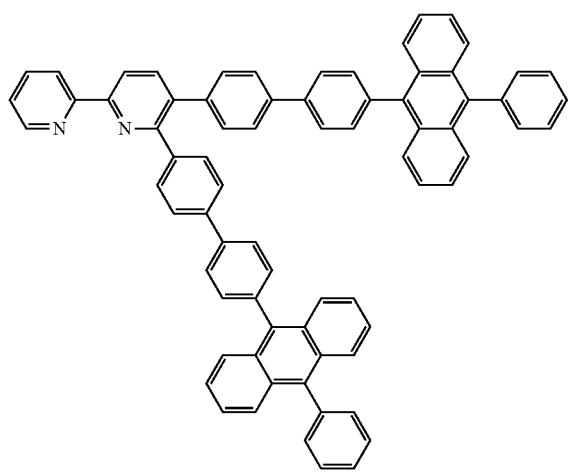

The bipyridine compounds represented by the above formulae have a high carrier-transport property and thus can be suitably used as a host material or a carrier-transport material for a light-emitting element. That is, another embodiment of the present invention is a light-emitting element material including the bipyridine compound represented by any of General Formulae (G1) to (G3), Structural Formula (100), and Structural Formula (106).

A light-emitting element manufactured using the bipyridine compound having the above structure can have high emission efficiency and low driving voltage. In other words, another embodiment of the present invention is a light-emitting element which includes a layer containing an organic compound between a pair of electrodes. The bipyridine compound is contained in the layer containing an organic compound. By application of current between the pair of electrodes, the light-emitting element emits light.

The light-emitting element including the bipyridine compound is used in a light-emitting module, so that the light-emitting module can have low power consumption. In other words, another embodiment of the present invention is a light-emitting module including the light-emitting element.

The light-emitting element including the bipyridine compound is used in a light-emitting device, so that the light-emitting device can have low power consumption. In other words, another embodiment of the present invention is a light-emitting device including the light-emitting element.

The light-emitting element including the bipyridine compound is used in a lighting device, so that the lighting device can have low power consumption. In other words, another embodiment of the present invention is a lighting device including the light-emitting element.

The light-emitting element including the bipyridine compound is used in a display device, so that the display device can have low power consumption. In other words, another embodiment of the present invention is a display device including the light-emitting element.

The light-emitting element including the bipyridine compound is used in an electronic device, so that the electronic device can have low power consumption. In other words, another embodiment of the present invention is an electronic device including the light-emitting element.

The bipyridine compound having any of the above structures is a substance having both a high carrier-transport property and a wide energy gap, and can be suitably used for a material contained in a transport layer or a host material or an emission center substance in a light-emitting layer in a light-emitting element. A light-emitting element using a light-emitting element material containing the bipyridine compound can be a light-emitting element having high emission efficiency. A light-emitting element including the bipyridine compound can have low driving voltage. The bipyridine compound can also be used as an organic semiconductor material. The bipyridine compound having any of the above structures has high heat resistance.

DETAILED DESCRIPTION OF THE INVENTION

Figure 1A:
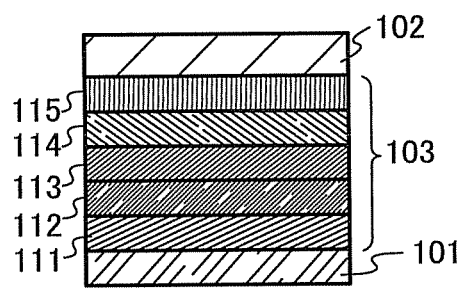
FIGS. 1A and 1B are conceptual diagrams of light-emitting elements.

Hereinafter, embodiments of the present invention will be described. It is easily understood by those skilled in the art that modes and details disclosed herein can be modified in various ways without departing from the spirit and scope of the present invention. Therefore, the present invention is not construed as being limited to description of the embodiments.

Embodiment 1

The present inventors have found that a light-emitting element having good characteristics can be obtained by using a bipyridine compound having at least one 2,2'-bipyridine structure and at least two anthracene skeletons as light-emitting element materials. In particular, the present inventors have found that a bipyridine compound in which an anthracene skeleton is bonded to each of the 5-position and the 6-position of 2,2'-bipyridine through an arylene group can be synthesized and a light-emitting element having good characteristics can be obtained in the case where the bipyridine compound is used as a light-emitting element material.

The bipyridine compound with any of the above structures has two anthracene skeletons and thus has a high carrier-transport property. With the use of the bipyridine compound for a carrier-transport layer (particularly, an electron-transport layer) of a light-emitting element, the light-emitting element can have good characteristics such as low driving voltage.

In addition, in the bipyridine compound with any of the above structures, a group bonding to the 5-position of bipyridine and a group bonding to the 6-position of the bipyridine are both hydrocarbon groups, and thus the bipyridine compound is a substance having high heat resistance. For this reason, a decrease in reliability of a light-emitting element manufactured with the use of the bipyridine compound or a device including such a light-emitting element, which is caused by deterioration of the bipyridine compound due to heat, hardly occurs, whereby a highly reliable light-emitting element or device can be achieved.

More specifically, the bipyridine compound with any of the above structures is a bipyridine compound represented by General Formula (G1).

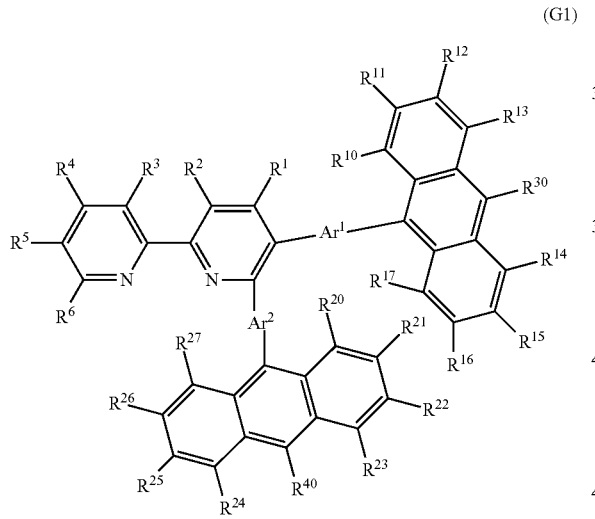

(G1)

Note that in the formula, $R^1$ to $R^6$, $R^{10}$ to $R^{17}$, and $R^{20}$ to $R^{27}$ each independently represent hydrogen or an alkyl group having 1 to 4 carbon atoms. Specific examples of the alkyl group having 1 to 4 carbon atoms are a methyl group, an ethyl group, a n-propyl group, an iso-propyl group, an n-butyl group, a sec-butyl group, an iso-butyl group, and a tert-butyl group. Examples of groups that can be used as $R^1$ to $R^6$, $R^{10}$ to $R^{17}$, and $R^{20}$ to $R^{27}$ are shown in Structural Formulae (R1-1) to (R1-9). Note that the groups that can be used as $R^1$ to $R^6$, $R^{10}$ to $R^{17}$, and $R^{20}$ to $R^{27}$ are not limited to these examples.

(R1-1)

(R1-2)

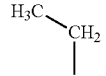

(R1-3)

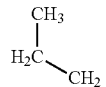

(R1-4)

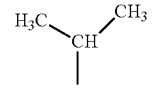

(R1-5)

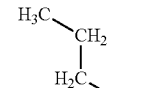

(R1-6)

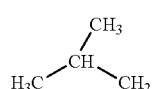

(R1-7)

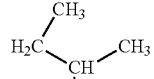

(R1-8)

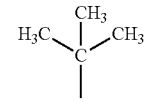

(R1-9)

$Ar^1$ and $Ar^2$ each independently represent an arylene group having 6 to 13 carbon atoms. Specific examples of the arylene group are a phenylene group, a naphthylene group, a biphenyl-diyl group, and a fluorene-diyl group. Note that each of these arylene groups may have a substituent, and the substituent can be an alkyl group having 1 to 4 carbon atoms, a phenyl group, or the like. In addition, these substituents may be bonded to one another to form a ring. For example, in the case where the arylene group is a fluorene-diyl group and a carbon atom at the 9-position of the fluorene skeleton is substituted with two phenyl groups, carbon atoms of the phenyl groups may be bonded to each other to form a spirofluorene skeleton. Examples of structures of $Ar^1$ and $Ar^2$ are shown in Structural Formulae (Ar-1) to (Ar-15). Note that groups that can be used as $Ar^1$ and $Ar^2$ are not limited to the following examples.

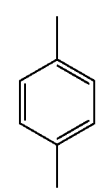

(Ar-1)

(Ar-2)
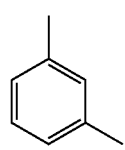
(Ar-3)
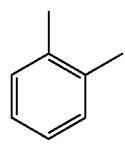
(Ar-4)
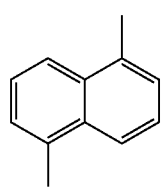
(Ar-5)
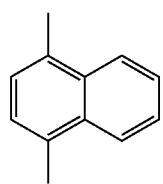
(Ar-6)
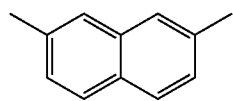
(Ar-7)
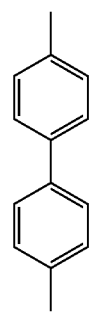
(Ar-8)
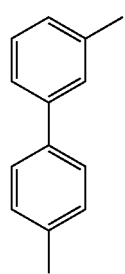
(Ar-9)
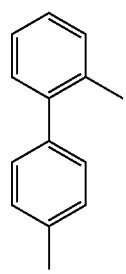
(Ar-10)
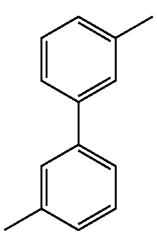
(Ar-11)
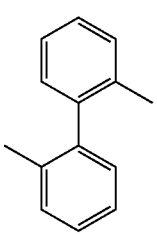
(Ar-12)
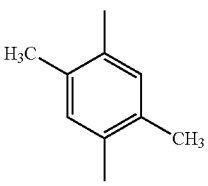
(Ar-13)
(Ar-14)

-continued

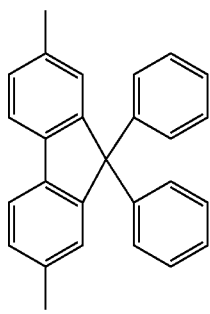
(Ar-15)

R$^{30}$ and R$^{40}$ each independently represent any of hydrogen, an alkyl group having 1 to 4 carbon atoms, and an aryl group having 6 to 13 carbon atoms. Specific examples of the aryl group are a phenyl group, a naphthyl group, a biphenyl group, and a fluorenyl group. Note that each of these aryl groups may have a substituent, and the substituent can be an alkyl group having 1 to 4 carbon atoms, a phenyl group, or the like. In addition, these substituents may be bonded to one another to form a ring. For example, in the case where the aryl group is a fluorenyl group and a carbon atom at the 9-position of the fluorene skeleton of this group is substituted with two phenyl groups, carbon atoms at the 2-positions of the phenyl groups are bonded to each other to form a spirofluorene skeleton. Examples of structures of R$^{30}$ and R$^{40}$ are shown in Structural Formulae (R2-1) to (R2-23). Note that groups that can be used as R$^{30}$ and R$^{40}$ are not limited to the following examples.

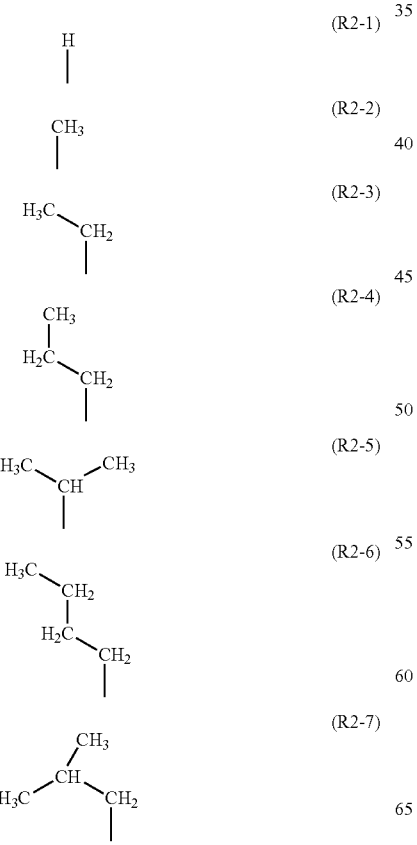

(R2-1)
(R2-2)
(R2-3)
(R2-4)
(R2-5)
(R2-6)
(R2-7)

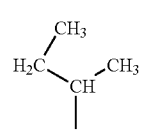
(R2-8)

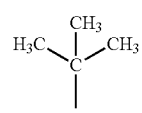
(R2-9)

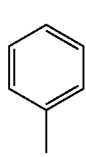
(R2-10)

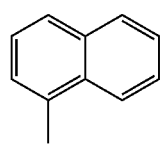
(R2-11)

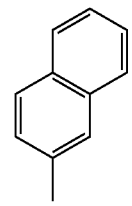
(R2-12)

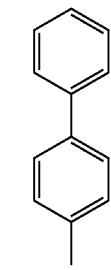
(R2-13)

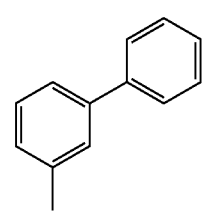
(R2-14)

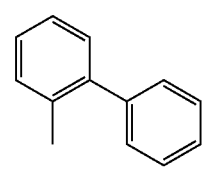
(R2-15)

-continued (R2-16)
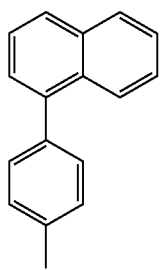

(R2-17)
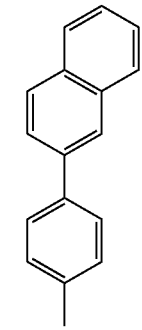

(R2-18)
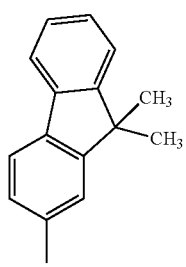

(R2-19)
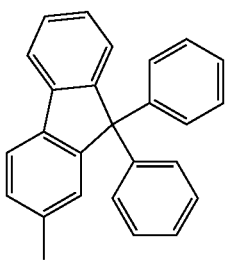

(R2-20)
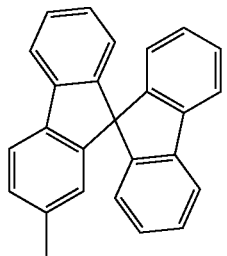

(R2-21)
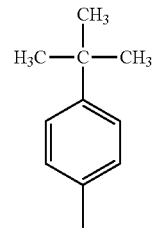

-continued (R2-22)
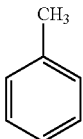

(R2-23)
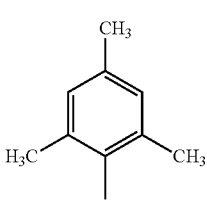

In the bipyridine compound represented by General Formula (G1), a structure in which all of $R^1$ to $R^6$ are hydrogen is preferable in terms of availability of a raw material and cost. That is, another embodiment of the present invention is a bipyridine compound represented by General Formula (G2).

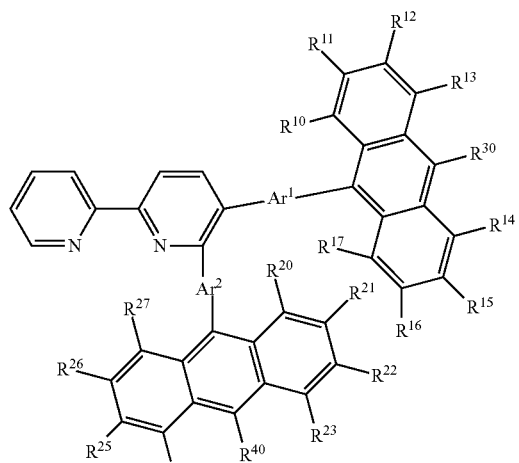

(G2)

Note that in General Formula (G2), $R^{10}$ to $R^{17}$ and $R^{20}$ to $R^{27}$ each independently represent hydrogen or an alkyl group having 1 to 4 carbon atoms; $Ar^1$ and $Ar^2$ each independently represent an arylene group having 6 to 13 carbon atoms; and $R^{30}$ and $R^{40}$ each independently represent any of hydrogen, an alkyl group having 1 to 4 carbon atoms, and an aryl group having 6 to 13 carbon atoms.

Specific examples of substituents that can be used as $R^{10}$ to $R^{17}$ and $R^{20}$ to $R^{27}$, specific examples of substituents that can be used as $Ar^1$ and $Ar^2$, and specific examples of substituents that can be used as $R^{30}$ and $R^{40}$ in General Formula (G2) correspond to the specific examples of substituents that can be used as $R^1$ to $R^6$, $R^{10}$ to $R^{17}$, and $R^{20}$ to $R^{27}$, the specific examples of substituents that can be used as $Ar^1$ and $Ar^2$, and the specific examples of substituents that can be used as $R^{30}$ and $R^{40}$ in General Formula (G1), respectively. Therefore, repetition of the explanation of the specific examples is avoided. Refer to the description of General Formula (G1).

In the bipyridine compound represented by General Formula (G2), a structure in which all of $R^{10}$ to $R^{17}$ and $R^{20}$ to $R^{27}$ are hydrogen is preferable in terms of availability of a raw material and cost. That is, another embodiment of the present invention is a bipyridine compound represented by General Formula (G3).

(G3)

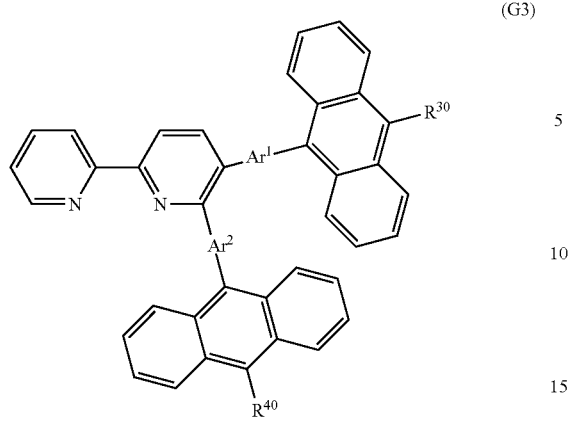

Note that in the formula, $Ar^1$ and $Ar^2$ each independently represent an arylene group having 6 to 13 carbon atoms; and $R^{30}$ and $R^{40}$ each independently represent any of hydrogen, an alkyl group having 1 to 4 carbon atoms, and an aryl group having 6 to 13 carbon atoms.

Specific examples of substituents that can be used as $Ar^1$ and $Ar^2$, and specific examples of substituents that can be used as $R^{30}$ and $R^{40}$ in General Formula (G3) correspond to the specific examples of substituents that can be used as $Ar^1$ and $Ar^2$, and the specific examples of substituents that can be used as $R^{30}$ and $R^{40}$ in General Formula (G1), respectively. Therefore, repetition of the explanation of the specific examples is avoided. Refer to the description of General Formula (G1).

Note that the bipyridine compound with the above structure is preferably a bipyridine compound in which $R^{30}$ and $R^{40}$ each independently represent an aryl group, and more preferably is a bipyridine compound in which $R^{30}$ and $R^{40}$ each independently represent a phenyl group or a biphenyl group.

The bipyridine compound with the above structure is preferably a bipyridine compound in which $Ar^1$ and $Ar^2$ each independently represent a phenylene group or a biphenyldiyl group.

Specific examples of the bipyridine compounds represented by General Formulae (G1) to (G3) include substances represented by Structural Formulae (100) to (129).

(100)

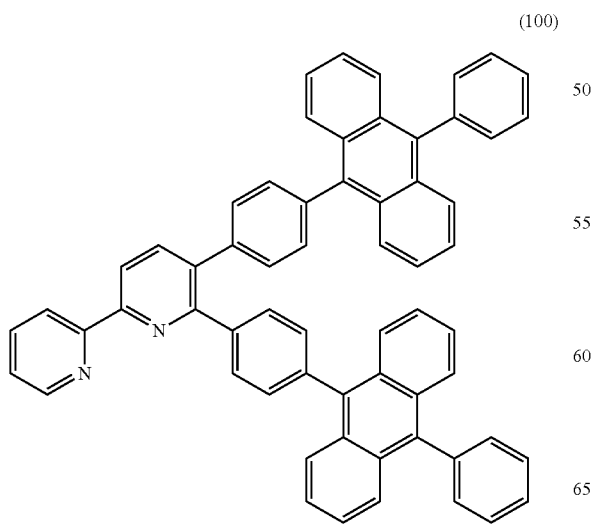

(101)

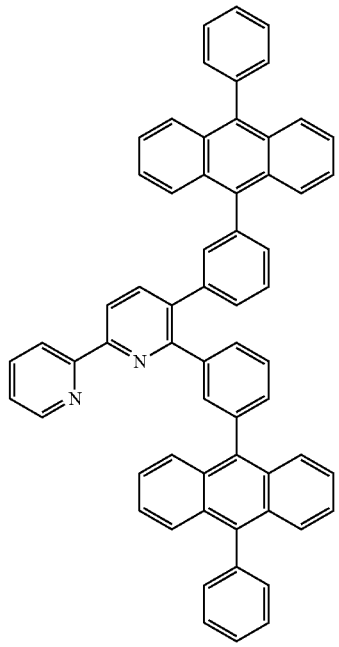

(102)

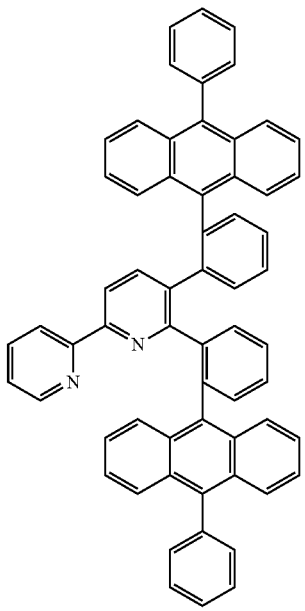

(103)
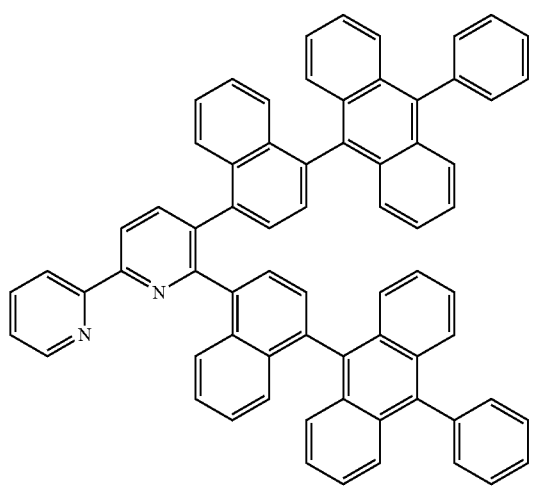
(105)
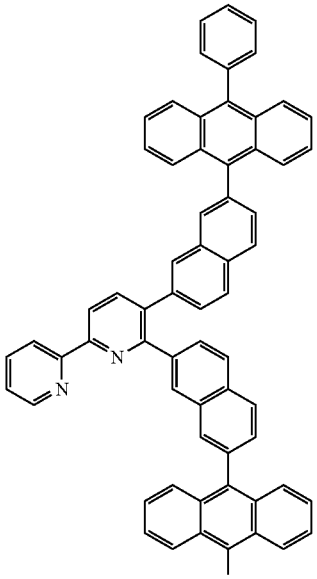
(104)
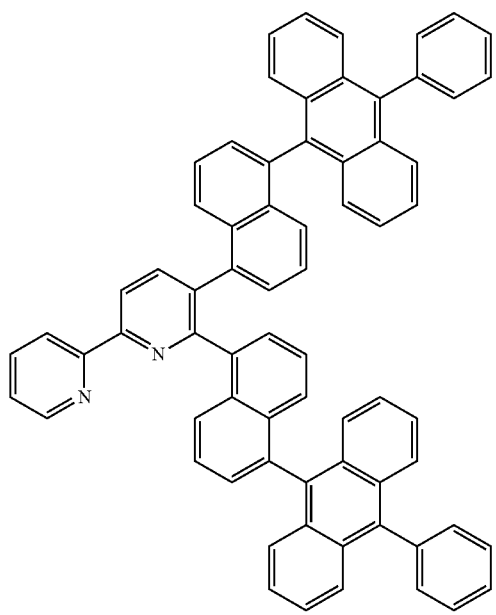
(106)
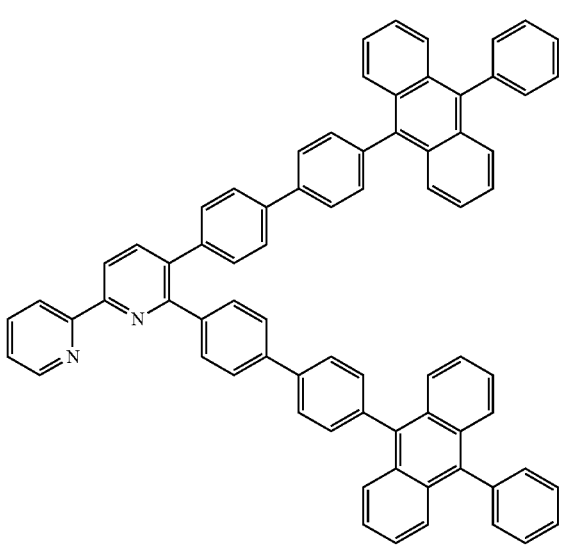

(107)
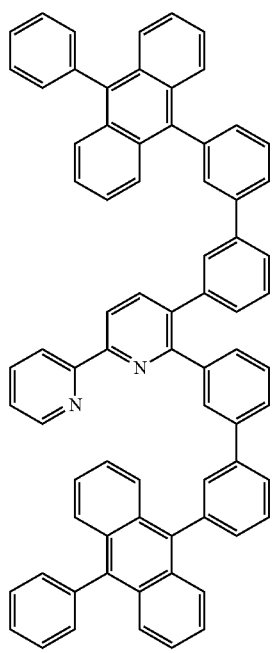
(108)
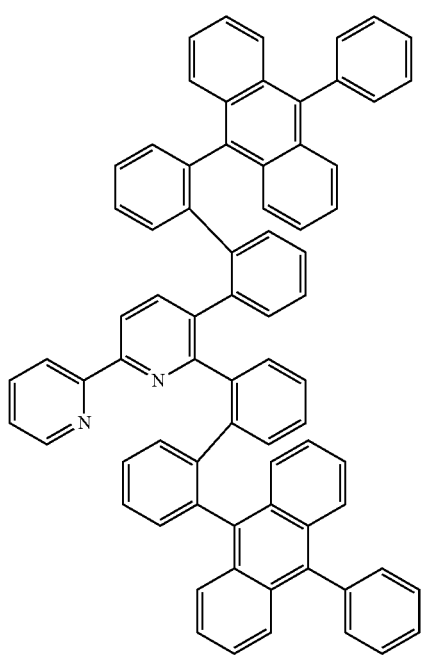
(109)
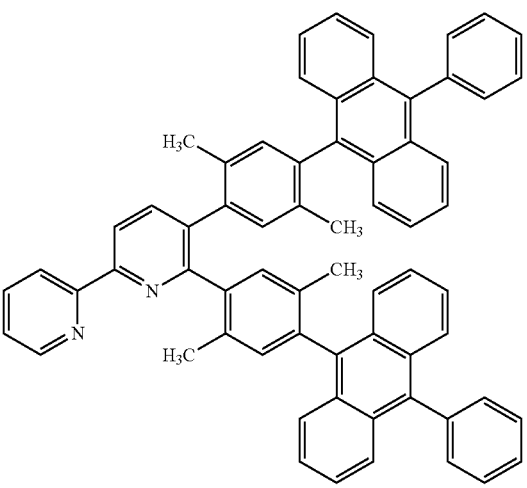
(110)
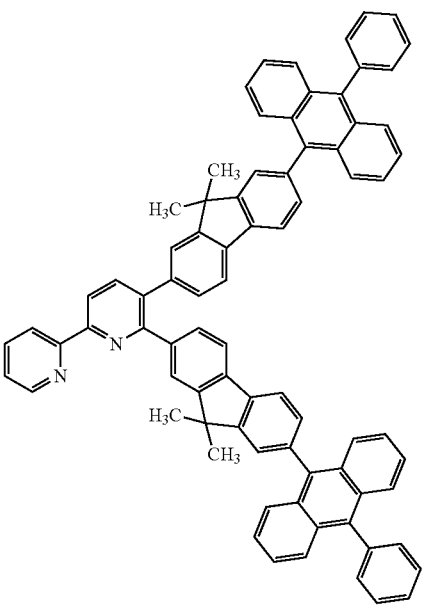

(111)
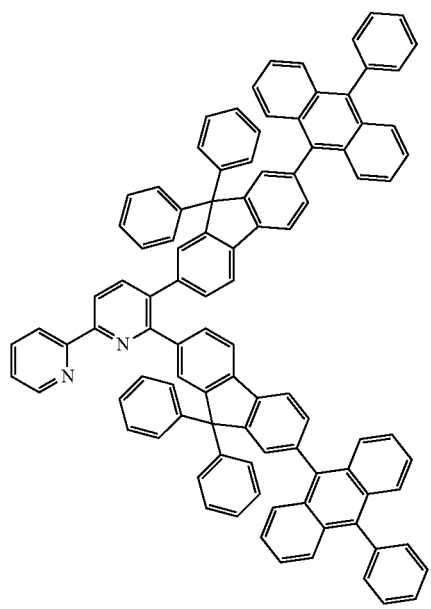
(112)
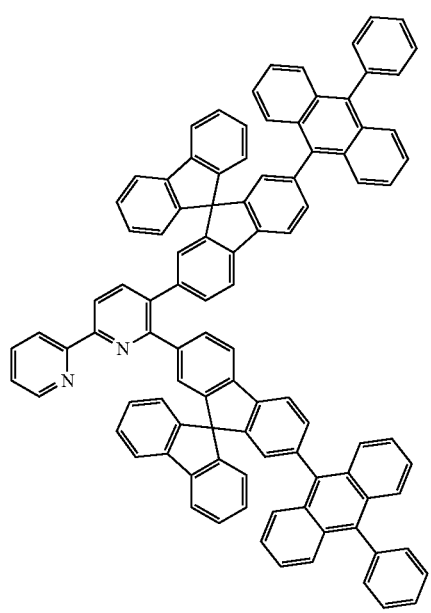
(113)
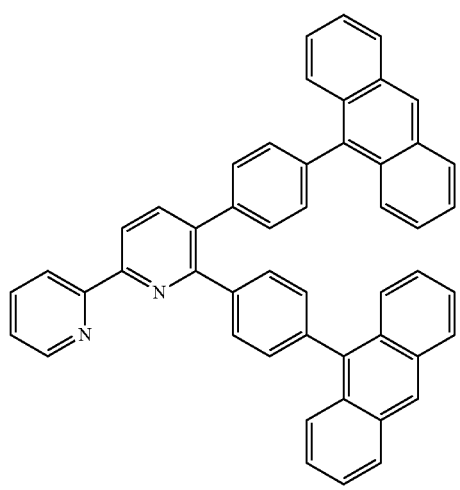
(114)
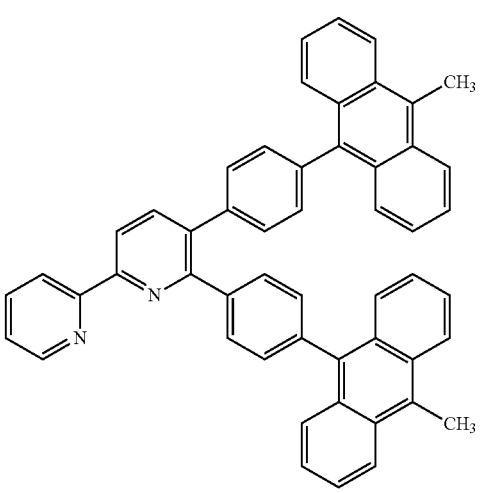
(115)
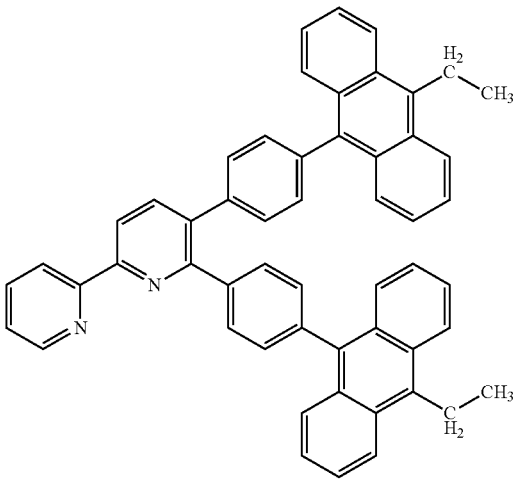

(116)
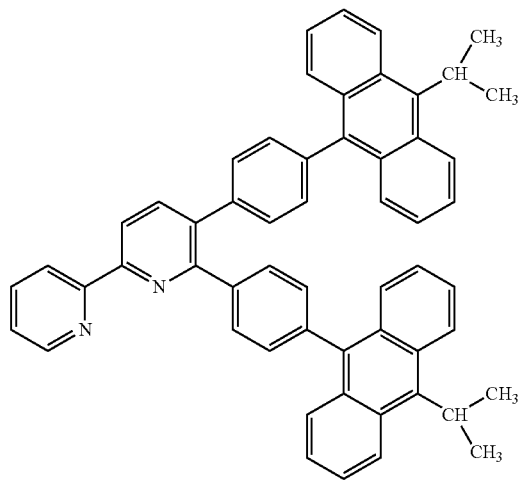
(117)
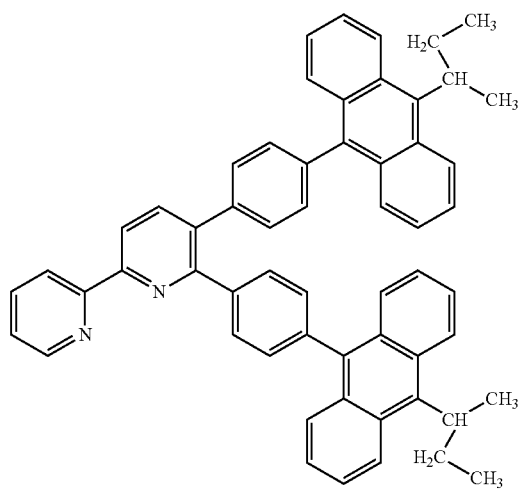
(118)
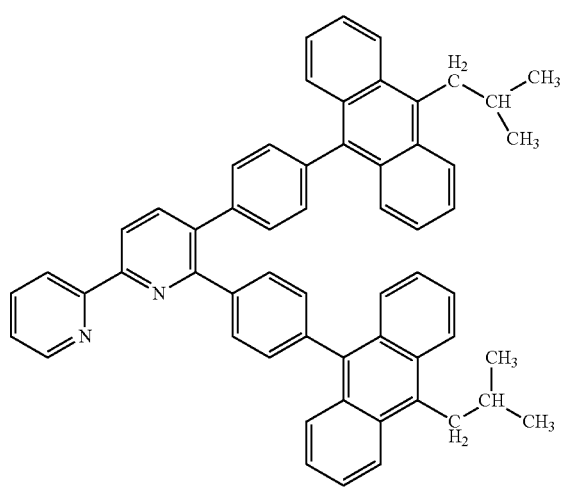
(119)
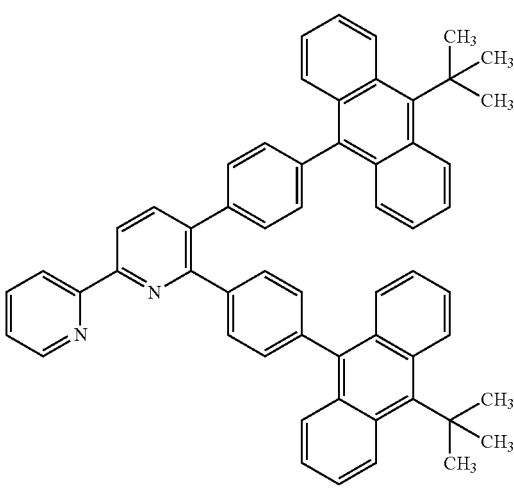
(120)
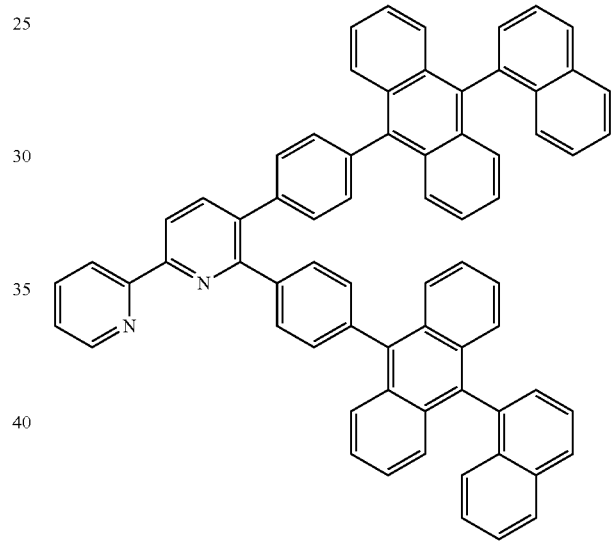
(121)
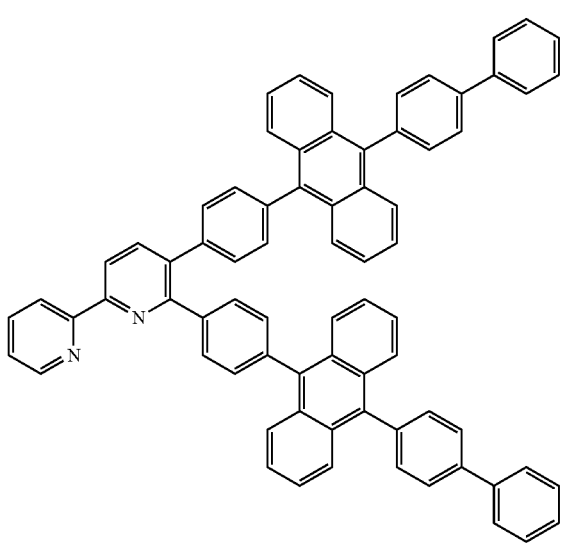

-continued
(122)
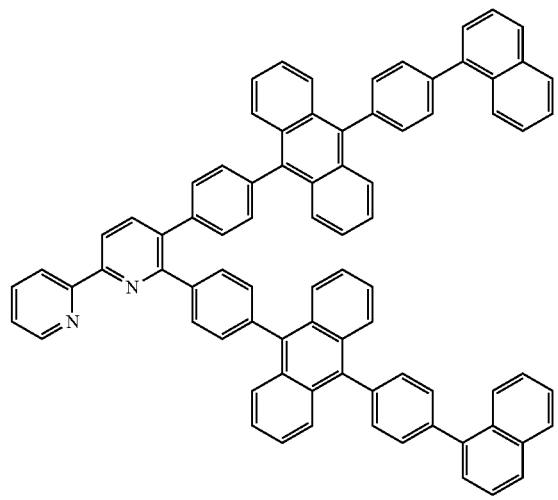
(123)
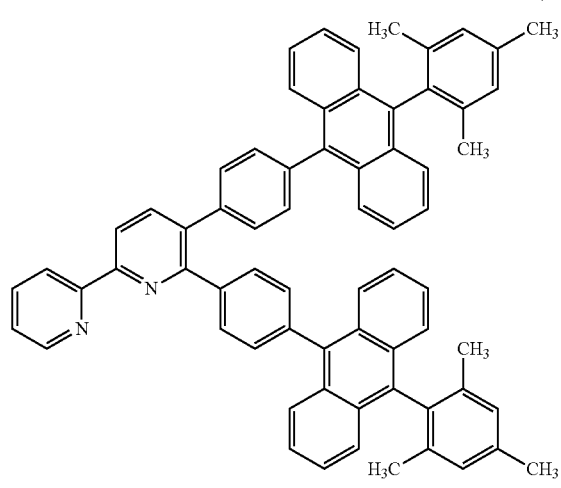
(124)
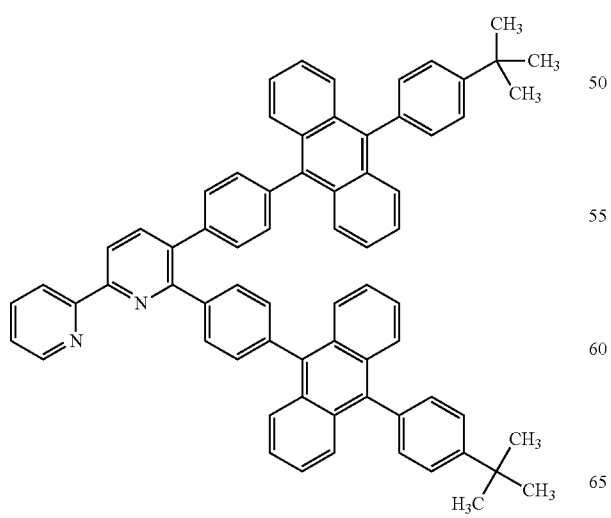
-continued
(125)
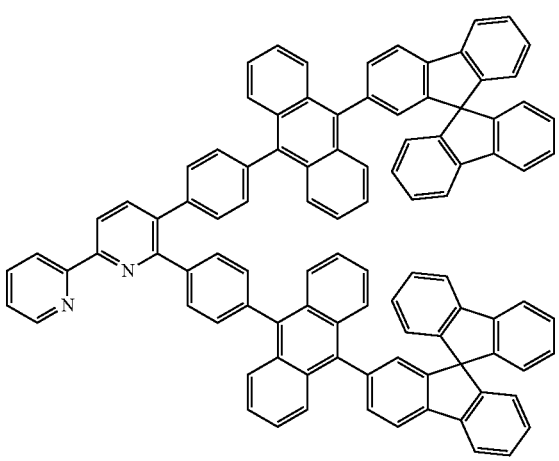
(126)
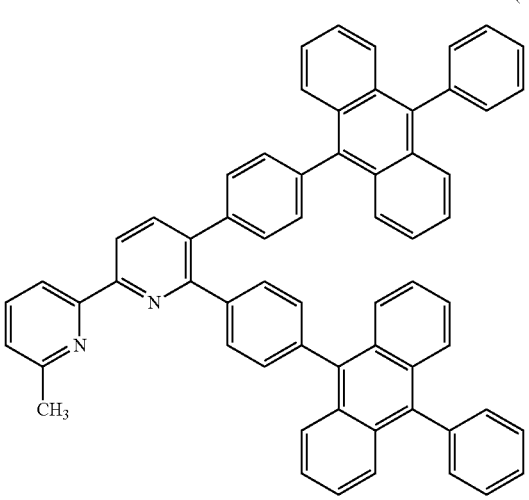
(127)
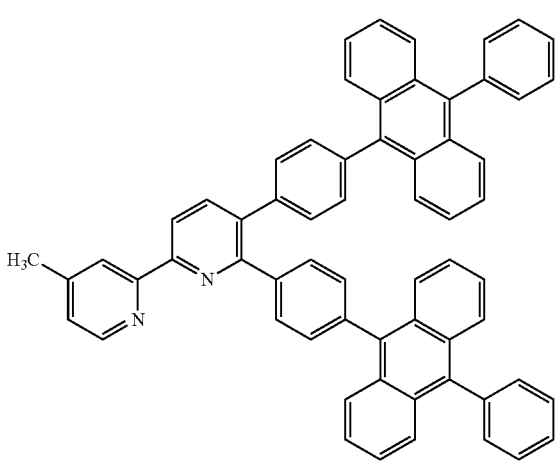

(128)

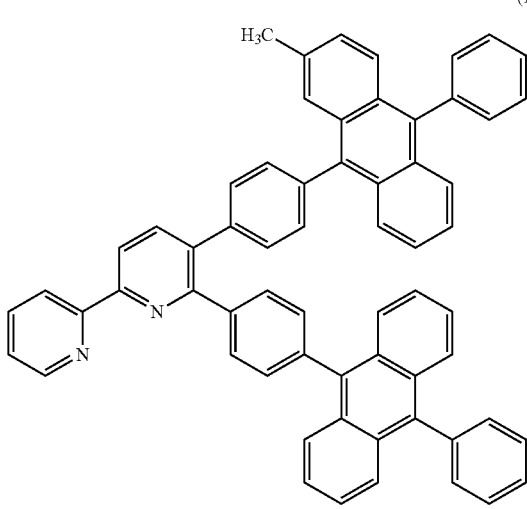

(129)

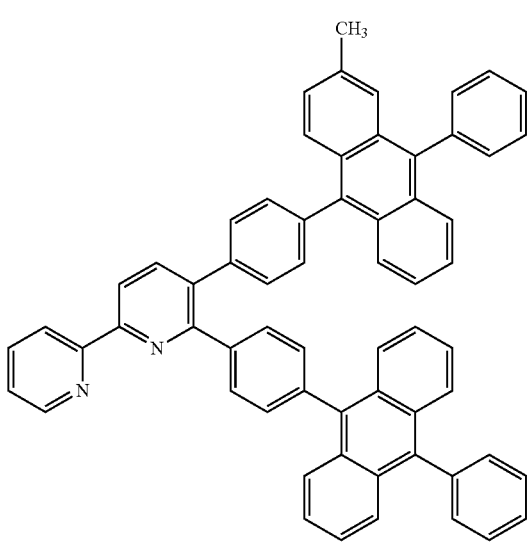

The above-described bipyridine compound has a high carrier-transport property and thus is suitably used for a carrier-transport material or a host material. Thus, a light-emitting element driven at low voltage can also be provided. Moreover, the bipyridine compound has a wide band gap and a high singlet level; thus, the bipyridine compound enables even a light-emitting element emitting blue fluorescence to efficiently emit light. Furthermore, the bipyridine compound is a material having high heat resistance.

Furthermore, the bipyridine compound in this embodiment can also be used as a light-emitting material which emits blue to violet light.

Next, a method for synthesizing the bipyridine compound represented by General Formula (G1) is described.

(G1)

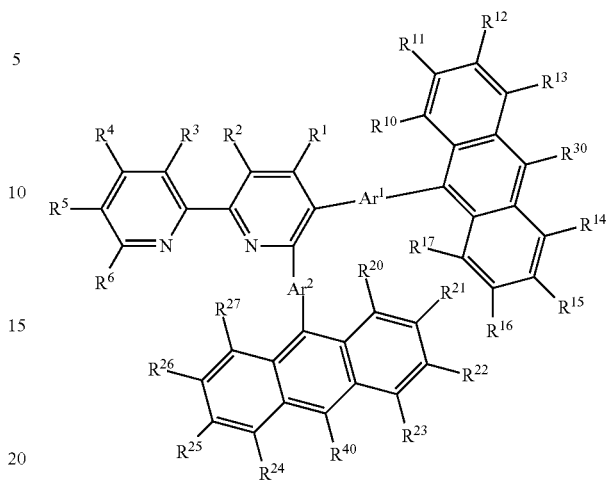

A variety of reactions can be applied to the method for synthesizing the bipyridine compound. For example, the bipyridine compound can be synthesized through a reaction shown in Synthesis Scheme (A-1). Note that in General Formula (G1) and Synthesis Scheme (A-1), $R^1$ to $R^6$, $R^{10}$ to $R^{17}$, and $R^{20}$ to $R^{27}$ each independently represent hydrogen or an alkyl group having 1 to 4 carbon atoms; $Ar^1$ and $Ar^2$ each independently represent an arylene group having 6 to 13 carbon atoms; and $R^{30}$ and $R^{40}$ each independently represent any of hydrogen, an alkyl group having 1 to 4 carbon atoms, and an aryl group having 6 to 13 carbon atoms. Specific examples of the substituents are already given; therefore, the description is omitted here.

(A-1)

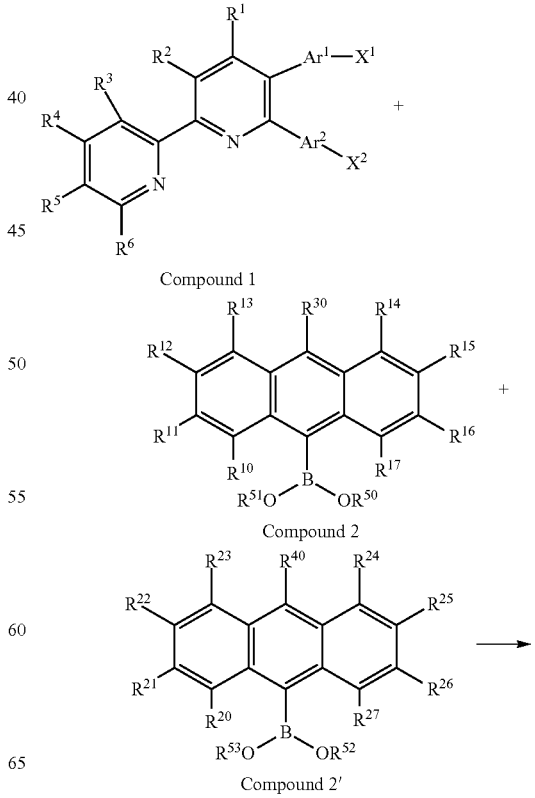

-continued

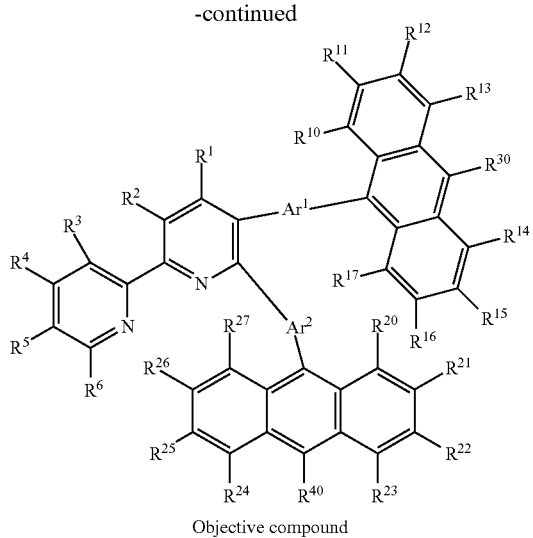

Objective compound

As shown in Synthesis Scheme (A-1), a halide of a 2,2'-bipyridine derivative or a 2,2'-bipyridine derivative that has a triflate group as a substituent (Compound 1) and an organoboron compound(s) of an anthracene derivative(s) and(or) a boronic acid(s) of an anthracene derivative(s) (Compound 2 and Compound 2') are coupled by a Suzuki-Miyaura reaction, thereby obtaining an objective compound. Note that $R^{50}$, $R^{51}$, $R^{52}$ and $R^{53}$ each independently represent any of hydrogen and an alkyl group having 1 to 6 carbon atoms. In Synthesis Scheme (A-1), $R^{50}$ and $R^{51}$, and $R^{52}$ and $R^{53}$ may be bonded to each other to form a ring. Furthermore, $X^1$ and $X^2$ each independently represent a halogen group or a triflate group.

Suzuki-Miyaura reaction is a coupling reaction in which palladium is used as a catalyst and an organoboron compound is used as a substrate in the presence of a base. Examples of compound that can be used as a palladium catalyst or a precursor thereof in Synthesis Scheme (A-1) include palladium (II)acetate, tetrakis(triphenylphosphine)palladium(0), and bis(triphenylphosphine)palladium(II)dichloride. Examples of ligands of the palladium catalyst include tri(ortho-tolyl)phosphine, triphenylphosphine, and tricyclohexylphosphine.

Examples of a base that can be used in Synthesis Scheme (A-1) include an organic base such as sodium tert-butoxide and an inorganic base such as potassium carbonate or sodium carbonate.

The reaction of Synthesis Scheme (A-1) can be performed in a solution. Examples of a solvent that can be used include, but not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of an ether such as ethylene glycol dimethyl ether and water. Note that a mixed solvent of toluene and water, a mixed solvent of toluene, ethanol, and water, or a mixed solvent of an ether such as ethylene glycol dimethyl ether and water is more preferable.

As the reaction for synthesizing the bipyridine compound represented by General Formula (G1), a cross coupling reaction using an organoaluminum compound, an organozirconium compound, an organozinc compound, an organotin compound, or the like can be employed other than the Suzuki-Miyaura reaction (Synthesis Scheme (A-1)) using the organoboron compound(s) and(or) the boronic acid(s) represented by Compound 2 and Compound 2'.

In the reaction shown in Synthesis Scheme (A-1), a halide of 2,2'-bipyridine derivative or a 2,2'-bipyridine derivative that has a triflate group as a substituent is coupled with the organoboron compound(s) of an anthracene derivative(s) and(or) the boronic acid(s) of an anthracene derivative(s); alternatively, an organoboron compound(s) of a 2,2'-bipyridine derivative or a boronic acid of a 2,2'-bipyridine derivative may be coupled with a halide of an anthracene derivative or an anthracene derivative that has a triflate group as a substituent by the Suzuki-Miyaura reaction.

In this manner, the bipyridine compound represented by General Formula (G1) can be synthesized.

Embodiment 2

In this embodiment, an example will be described in which the bipyridine compound described in Embodiment 1 is used for an active layer of a vertical transistor (SIT) that is a kind of an organic semiconductor element.

Figure 2:
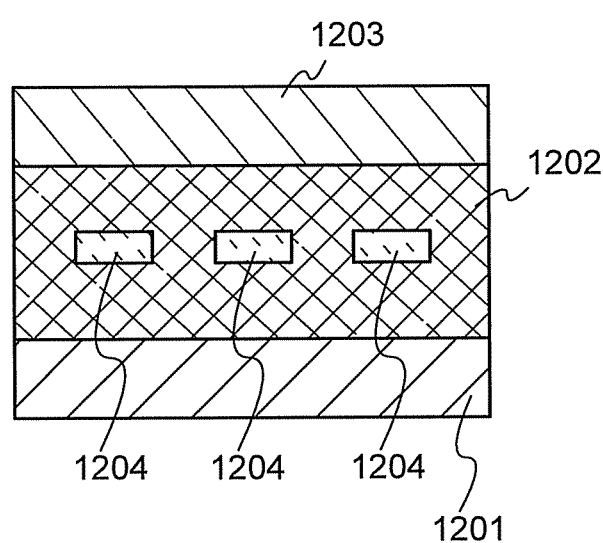
FIG. 2 is a conceptual diagram of an organic semiconductor element.

The element has a structure in which a thin-film active layer 1202 containing any of the bipyridine compounds described in Embodiment 1 is interposed between a source electrode 1201 and a drain electrode 1203, and gate electrodes 1204 are embedded in the active layer 1202, as illustrated in FIG. 2. The gate electrodes 1204 are electrically connected to a unit for applying gate voltage, and the source electrode 1201 and the drain electrode 1203 are electrically connected to a unit for controlling the voltage between the source and the drain.

In such an element structure, when voltage is applied between the source and the drain under the condition where gate voltage is not applied, current flows (on state). Then, by application of voltage to the gate electrode in that state, a depletion layer is formed in the periphery of the gate electrode 1204, and the current ceases flowing (off state). With such a mechanism, the element operates as a transistor.

Like a light-emitting element, a vertical transistor should contain a material that can achieve both a high carrier-transport property and favorable film quality for an active layer; the bipyridine compound described in Embodiment 1 meets such a requirement and therefore can be suitably used.

Embodiment 3

In this embodiment, one embodiment of a light-emitting element using any of the bipyridine compounds described in Embodiment 1 will be described with reference to FIG. 1A. In the light-emitting element described in this embodiment, the substance is used as at least one of a host material, a light-emitting material, and an electron-transport material.

A light-emitting element of this embodiment has a plurality of layers between a pair of electrodes. In this embodiment, the light-emitting element includes a first electrode 101, a second electrode 102, and a layer 103 containing an organic compound, which is provided between the first electrode 101 and the second electrode 102. Note that in this embodiment, the first electrode 101 functions as an anode and the second electrode 102 functions as a cathode. In other words, when voltage is applied between the first electrode 101 and the second electrode 102 such that the potential of the first electrode 101 is higher than that of the second electrode 102, light emission can be obtained.

For the first electrode 101, any of metals, alloys, electrically conductive compounds, and mixtures thereof which have a high work function (specifically, a work function of 4.0 eV or more) or the like is preferably used. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Films of these electrically conductive metal oxides are usually formed by sputtering but may be formed by a sol-gel method or the like. For example, indium oxide-zinc oxide can be formed by a sputtering method using a target in which zinc oxide is added to indium oxide at 1 wt % to 20 wt %. Moreover, indium oxide containing tungsten oxide and zinc oxide (IWZO) can be formed by a sputtering method using a target in which tungsten oxide is added to indium oxide at 0.5 wt % to 5 wt % and zinc oxide is added to indium oxide at 0.1 wt % to 1 wt %. Other examples are gold (Au), platinum (Pt), nickel (Ni), tungsten (W), chromium (Cr), molybdenum (Mo), iron (Fe), cobalt (Co), copper (Cu), palladium (Pd), and a nitride of a metal material (such as titanium nitride). Graphene may also be used.

There is no particular limitation on the stacked structure of the layer 103 containing an organic compound. The layer 103 containing an organic compound can be formed by combining a layer containing a substance having an electron-transport property, a layer containing a substance having a hole-transport property, a layer containing a substance having an electron-injection property, a layer containing a substance having a hole-injection property, a layer containing a bipolar substance (a substance having an electron-transport property and a hole-transport property), a layer having a carrier-blocking property, and the like as appropriate. In this embodiment, the layer 103 containing an organic compound has a structure in which a hole-injection layer 111, a hole-transport layer 112, a light-emitting layer 113, an electron-transport layer 114, and an electron-injection layer 115 are stacked in this order over the first electrode 101 functioning as an anode. Materials contained in the layers are specifically given below.

The hole-injection layer 111 is a layer containing a substance having a hole-injection property. The hole-injection layer 111 can be formed using molybdenum oxide, vanadium oxide, ruthenium oxide, tungsten oxide, manganese oxide, or the like. The hole-injection layer 111 can also be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD); a high molecule compound such as poly(ethylenedioxythiophene)/poly(styrenesulfonic acid) (PEDOT/PSS), or the like.

The hole-injection layer 111 can be formed using a composite material in which a substance exhibiting an electron-accepting property (hereinafter, simply referred to as "electron-accepting substance") with respect to a substance having a hole-transport property is contained in the substance having a hole-transport property. In this specification, the composite material does not simply refer to a material in which two materials are mixed but a material in the state where charge transfer between the materials can be caused by a mixture of a plurality of materials. This charge transfer includes charge transfer that can occur only when there is an auxiliary effect of an electric field.

Note that by using the material in which the electron-accepting substance is contained in the substance having a hole-transport property, a material used for forming the electrode can be selected regardless of the work function of the electrode. In other words, besides a material having a high work function, a material having a low work function can be used for the first electrode 101. Examples of the electron-accepting substance include 7,7,8,8-tetracyano-2,3,5,6-tetrafluoroquinodimethane (abbreviation: $F_4$-TCNQ) and chloranil. A transition metal oxide can also be used. In particular, an oxide of a metal belonging to any of Groups 4 to 8 of the periodic table can be suitably used. Specifically, vanadium oxide, niobium oxide, tantalum oxide, chromium oxide, molybdenum oxide, tungsten oxide, manganese oxide, and rhenium oxide are preferable because of their electron-accepting properties. Among these, molybdenum oxide is especially preferable as the electron-accepting substance because it is stable in the atmosphere, has a low hygroscopic property, and is easily handled.

As the substance having a hole-transport property used for the composite material, any of a variety of organic compounds such as an aromatic amine compound, a carbazole compound, an aromatic hydrocarbon, and a high molecular compound (such as an oligomer, a dendrimer, or a polymer) can be used. The organic compound used for the composite material is preferably an organic compound having a high hole-transport property. Specifically, a substance having a hole mobility of $1 \times 10^{-6}$ $cm^2/Vs$ or higher is preferably used. Note that any other substance may be used as long as the substance has a hole-transport property higher than an electron-transport property. Specific examples of the organic compound that can be used as a substance having a hole-transport property in the composite material are given below.

Examples of the aromatic amine compound include N,N'-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Specific examples of the carbazole compound that can be used for the composite material include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples of the carbazole compound that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene.

Examples of the aromatic hydrocarbon that can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples are pentacene and coronene. As these aromatic hydrocarbons given here, it is preferable that an aromatic hydrocarbon having a hole mobility of 1×10$^{-6}$ $^2$/Vs or more and having 14 to 42 carbon atoms be used.

The aromatic hydrocarbon that can be used for the composite material may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

The hole-transport layer 112 is a layer containing a substance having a hole-transport property. As the substance having a hole-transport property, those given above as the substances having hole-transport properties, which can be used for the above composite material, can also be used. Note that a detailed description is omitted to avoid repetition. Refer to the description of the composite material.

The light-emitting layer 113 is a layer containing a light-emitting substance. The light-emitting layer 113 may be formed using a film containing only a light-emitting substance or a film in which an emission center substance is dispersed in a host material.

There is no particular limitation on a material that can be used as the light-emitting substance or the emission center substance in the light-emitting layer 113, and light emitted from the material may be either fluorescence or phosphorescence. Examples of the above light-emitting substance or emission center substance are fluorescent substances and phosphorescent substances. Examples of the fluorescent substance include N,N'-bis[4-(9-phenyl-9H-fluoren-9-yl)phenyl]-N,N'-diphenyl-pyrene-1,6-diamine (abbreviation: 1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N''',N''''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-[2-isopropyl-6-[2-(1,1,7,7-tetramethyl-2,3,6,7-tetrahydro-1H,5H-benzo[ij]quinolizin-9-yl)ethenyl]-4H-pyran-4-ylidene]propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJ™). Examples of the phosphorescent substance include bis[2-(3',5'-bistrifluoromethylphenyl)pyridinato-N,C$^{2'}$]iridium(III) picolinate (abbreviation: Ir(CF$_3$ ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), tris(acetylacetonato) (monophenanthroline)terbium(III) (abbreviation: Tb(acac)$_3$(Phen)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), bis[2-(2'-benzo[4,5-α]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphyrin platinum(II) (abbreviation: PtOEP), tris(1,3-diphenyl-1,3-propanedionato) (monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)). Note that a bipyridine compound according to one embodiment of the present invention, a typical example of which is the bipyridine compound represented by General Formula (G1) described in Embodiment 1, emits light in the blue to ultraviolet region, and therefore can also be used as an emission center substance.

The bipyridine compound which is described in Embodiment 1 and represented by General Formula (G1) has a wide band gap; thus, the bipyridine compound can be suitably used as a host material in which an emission center substance emitting blue fluorescence is dispersed. Needless to say, the bipyridine compound can also be used as a host material in which an emission center substance emitting fluorescence with a wavelength longer than that of blue light is dispersed. The bipyridine compound has a high electron-transport property and thus can be suitably used as a material contained in the carrier-transport layer adjacent to the light-emitting layer. Since the bipyridine compound has a wide band gap, the energy of carriers that recombine in the host material can be efficiently transferred to an emission center substance even if the emission center substance is a substance that emits blue fluorescence. Thus, a light-emitting element having high emission efficiency can be manufactured. Note that in the case where the bipyridine compound which is described in Embodiment 1 and represented by General Formula (G1) is used as a host material, an emission center substance is preferably selected from, but not limited to, substances having a narrower band gap or a lower singlet level or triplet level than the bipyridine compound.

Furthermore, the bipyridine compounds described in Embodiment 1 each have a high carrier-transport property. Thus, the use of the bipyridine compound as a host material allows a light-emitting element driven at low voltage to be manufactured.

When the bipyridine compound represented by General Formula (G1) is not used as the host material described above, any of the following substances can be used for the host material: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenylamino]biphenyl (abbreviation: BSPB). Other examples are condensed polycyclic aromatic compounds such as anthracene derivatives, phenanthrene derivatives, pyrene derivatives, chrysene derivatives, and dibenzo[g,p]chrysene derivatives. Specific examples thereof are 9,10-diphenylanthracene (abbreviation: DPAnth), N,N'-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetramine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 3,3',3''-(benzene-1,3,5-triyl)tripyrene (abbreviation: TPB3). Other than these, known materials can be given.

The light-emitting layer 113 may be a stack of two or more layers. For example, in the case where the light-emitting layer 113 is formed by stacking a first light-emitting layer and a second light-emitting layer in this order over the hole-transport layer, a structure can be employed in which the first light-emitting layer serves as a layer having a hole-transport property and the second light-emitting layer serves as a layer having an electron-transport property.

In the case where the light-emitting layer having the above-described structure includes a plurality of materials, co-evaporation by a vacuum evaporation method can be used, or alternatively an inkjet method, a spin coating method, a dip coating method, or the like with a solution of the materials can be used.

The electron-transport layer 114 is a layer containing a substance having a high electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Ahnq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq), or the like. A metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones having an electron mobility of $10^{-6}$ cm$^2$/Vs or higher. Note that any substance other than the above substances may be used for the electron-transport layer as long as the substance has an electron-transport property higher than a hole-transport property.

The bipyridine compounds described in Embodiment 1 are preferably used as a material contained in the electron-transport layer 114. The bipyridine compounds described in Embodiment 1 each have a wide band gap and thus can effectively prevent transfer of excitation energy in the light-emitting layer to the electron-transport layer 114 to suppress a reduction in emission efficiency due to the excitation energy transfer, and allow a light-emitting element having high emission efficiency to be manufactured. Moreover, the bipyridine compounds described in Embodiment 1 each have a high carrier-transport property; thus, a light-emitting element driven at low voltage can be provided.

The electron-transport layer is not limited to a single layer and may be a stack of two or more layers containing any of the above substances.

A layer for controlling transport of electron carriers may be provided between the electron-transport layer and the light-emitting layer. This is a layer formed by addition of a small amount of a substance having a high electron-trapping property to a material having a high electron-transport property described above, and the layer is capable of adjusting carrier balance by suppressing transfer of electron carriers. Such a structure is very effective in preventing a problem (such as a reduction in element lifetime) caused when electrons pass through the light-emitting layer.

In addition, an electron-injection layer 115 may be provided in contact with the second electrode 102, between the electron-transport layer 114 and the second electrode 102. For the electron-injection layer 115, an alkali metal, an alkaline earth metal, or a compound thereof such as lithium, calcium, lithium fluoride (LiF), cesium fluoride (CsF), or calcium fluoride (CaF$_2$) can be used. A composite material of a substance having an electron-transport property and a substance exhibiting an electron-donating property (hereinafter, simply referred to as "electron-donating substance") with respect to the substance having an electron-transport property can also be used. Examples of the electron-donating substance include alkali metals, alkaline earth metals, and compounds thereof. For example, as the composite material, a composite material in which magnesium (Mg) is contained in Alq, or the like can be used. Note that a layer which is formed using a substance having an electron-transport property and contains an alkali metal or an alkaline earth metal is preferably used for the electron-injection layer 115, in which case electrons are efficiently injected from the second electrode 102. With such a structure, a conductive material as well as a substance having a low work function can be used for the cathode.

For the second electrode 102, any of metals, alloys, electrically conductive compounds, and mixtures thereof which have a low work function (specifically, a work function of 3.8 eV or less), and the like can be used. Specific examples of such a cathode material include elements belonging to Groups 1 or 2 in the periodic table such as lithium (Li), cesium (Cs), magnesium (Mg), calcium (Ca), and strontium (Sr), alloys containing any of the metals (e.g., MgAg or AlLi), rare earth metals such as europium (Eu) and ytterbium (Yb), alloys containing any of the metals, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a sputtering method, an ink-jet method, a spin coating method, or the like.

Furthermore, any of a variety of methods can be employed for forming the layer 103 containing an organic compound regardless of a dry process or a wet process. For example, a vacuum evaporation method, an ink-jet method, or a spin coating method may be employed. A different formation method may be employed for each electrode or each layer.

The electrode may be formed by a wet process using a sol-gel method, or by a wet process using paste of a metal material. Alternatively, the electrode may be formed by a dry process such as a sputtering method or a vacuum evaporation method.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light is extracted through the first electrode 101. In contrast, in the case where only the second electrode 102 is a light-transmitting electrode, light is extracted through the second electrode 102. In the case where both the first electrode 101 and the second electrode 102 are light-transmitting electrodes, light is extracted through the first electrode 101 and the second electrode 102.

The structure of the layers provided between the first electrode 101 and the second electrode 102 is not limited to the above-described structure. However, it is preferable that a light-emitting region where holes and electrons recombine be positioned away from the first electrode 101 and the second electrode 102 so as to prevent quenching due to the proximity of the light-emitting region and a metal used for an electrode or a carrier-injection layer.

Furthermore, to suppress transfer of energy from an exciton generated in the light-emitting layer, it is preferable that the hole-transport layer and the electron-transport layer which are in direct contact with the light-emitting layer, particularly a carrier-transport layer in contact with a side closer to the light-emitting region in the light-emitting layer 113 be formed using a substance having a wider energy gap than the light-emitting substance of the light-emitting layer or the emission center substance contained in the light-emitting layer.

Since the light-emitting element of this embodiment is formed using any of the bipyridine compounds described in Embodiment 1, which has a wide energy gap, as a host material and/or for the electron-transport layer, efficient light emission can be obtained even when an emission center substance has a wide energy gap and emits blue fluorescence, and the light-emitting element can have high emission efficiency. Thus, a light-emitting element with lower power consumption can be provided. In addition, light emission from a host material or a material contained in a carrier-transport layer is unlikely to occur; thus, a light-emitting element that provides light emission with high color purity can be provided. Furthermore, the bipyridine compounds described in Embodiment 1 each have a high carrier-transport property; thus, a light-emitting element driven at low voltage can be provided.

Such a light-emitting element may be manufactured using a substrate made of glass, plastic, or the like as a support. A plurality of such light emitting elements is formed over one substrate, thereby forming a passive matrix light emitting device. Alternatively, a transistor may be formed over a substrate made of glass, plastic, or the like, and the light-emitting element may be manufactured over an electrode electrically connected to the transistor. In this manner, an active matrix light-emitting device in which the driving of the light-emitting element is controlled by the transistor can be manufactured. Note that a structure of the transistor is not particularly limited. Either a staggered TFT or an inverted staggered TFT may be employed. In addition, the crystallinity of a semiconductor used for the TFT is not particularly limited. In addition, a driver circuit formed in a TFT substrate may be formed with n-type TFTs and p-type TFTs, or with either n-type TFTs or p-type TFTs. The semiconductor layer for forming the TFTs may be formed using any material as long as the material exhibits semiconductor characteristics; for example, an element belonging to Group 14 of the periodic table such as silicon (Si) and germanium (Ge), a compound such as gallium arsenide or indium phosphide, and an oxide such as zinc oxide or tin oxide can be used. For the oxide exhibiting semiconductor characteristics (oxide semiconductor), composite oxide of an element selected from indium, gallium, aluminum, zinc, and tin can be used. Examples thereof include zinc oxide (ZnO), indium oxide containing zinc oxide, and oxide containing indium oxide, gallium oxide, and zinc oxide. An organic semiconductor may also be used. The semiconductor layer may have either a crystalline structure or an amorphous structure. Specific examples of the crystalline semiconductor layer are a single crystal semiconductor, a polycrystalline semiconductor, and a microcrystalline semiconductor.

Embodiment 4

In this embodiment, an embodiment of a light-emitting element with a structure in which a plurality of light-emitting units are stacked (hereinafter, also referred to as "stacked-type element") will be described with reference to FIG. 1B. This light-emitting element is a light-emitting element including a plurality of light-emitting units between a first electrode and a second electrode. One light-emitting unit has the same structure as the layer 103 containing an organic compound which is described in Embodiment 3. In other words, the light-emitting element described in Embodiment 3 includes one light-emitting unit while the light-emitting element in this embodiment includes a plurality of light-emitting units.

Figure 1B:
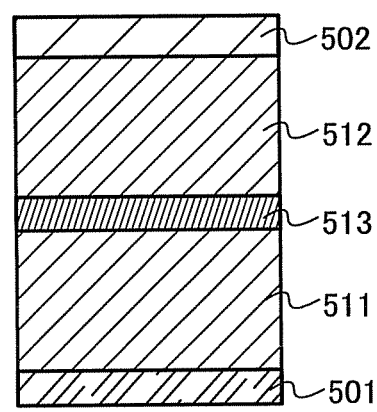

In FIG. 1B, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 in Embodiment 3, and materials described in Embodiment 3 can be used. Furthermore, the first light-emitting unit 511 and the second light-emitting unit 512 may have the same structure or different structures.

The charge-generation layer 513 contains a composite material of an organic compound and a metal oxide. This composite material of an organic compound and a metal oxide is the composite material which can be used for the hole-injection layer as described in Embodiment 3, and contains an organic compound and a metal oxide such as vanadium oxide, molybdenum oxide, or tungsten oxide. As the organic compound, a variety of compounds such as an aromatic amine compound, a bipyridine compound, an aromatic hydrocarbon, and a high molecular compound (such as an oligomer, a dendrimer, or a polymer) can be used. An organic compound having a hole mobility of $1 \times 10^{-6}$ cm$^2$/Vs or higher is preferably used as a hole-transport organic compound. However, any other substance may be used as long as the substance has a hole-transport property higher than an electron-transport property. The composite material of an organic compound and a metal oxide has a high carrier-injection property and a high carrier-transport property; thus, low-voltage driving and low-current driving can be achieved.

The charge-generation layer 513 may have a stacked-layer structure of a layer containing the composite material of an organic compound and a metal oxide and a layer containing another material. For example, a layer containing the composite material of an organic compound and a metal oxide may be combined with a layer containing a compound of a substance selected from electron-donating substances and a compound having a high electron-transport property. Moreover, the charge-generation layer 513 may be formed by combining a layer containing the composite material of an organic compound and a metal oxide with a transparent conductive film.

The charge-generation layer 513 provided between the first light-emitting unit 511 and the second light-emitting unit 512 may have any structure as far as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as far as the layer injects electrons into the first light-emitting unit 511 and holes into the second light-emitting unit 512 when a voltage is applied such that the voltage of the first electrode is higher than that of the second electrode.

Although the light-emitting element having two light-emitting units is described in this embodiment, the present invention can be similarly applied to a light-emitting element in which three or more light-emitting units are stacked. With a plurality of light-emitting units partitioned by the charge-generation layer between a pair of electrodes as in the light-emitting element according to this embodiment, it is possible to provide a light-emitting element which can emit light with high luminance with the current density kept low and has a long lifetime. Moreover, a light-emitting device which is driven at low voltage and consumes lower power can be achieved.

Furthermore, when emission colors of the light-emitting units are made different, light emission having a desired color can be obtained from the light-emitting element as a whole. For example, in the light-emitting element having two light-emitting units, when an emission color of the first light-emitting unit and an emission color of the second light-emitting unit are made to be complementary colors, it is possible to obtain a light-emitting element from which white light is emitted from the whole light-emitting element. Note that "complementary colors" refer to colors that can produce an achromatic color when mixed. In other words, when lights obtained from substances which emit complementary colors are mixed, white emission can be obtained. This can be applied to a light-emitting element having three light-emitting units. For example, when the first light-emitting unit emits red light, the second light-emitting unit emits green light, and the third light-emitting unit emits blue light, white light can be emitted from the whole light-emitting element.

The light-emitting element of this embodiment includes any of the bipyridine compounds described in Embodiment 1 and thus can have high emission efficiency. In addition, the light-emitting element can have low driving voltage. In addition, the light-emitting unit containing the bipyridine compound can provide light with high color purity, which originates from the emission center substance; therefore, it is easy to adjust the color of light emitted from the light-emitting element as a whole.

Note that this embodiment can be combined with any of the other embodiments as appropriate.

Embodiment 5

In this embodiment, a display module including a light-emitting element including any of the bipyridine compounds described in Embodiment 1 will be described.

Figure 3A:
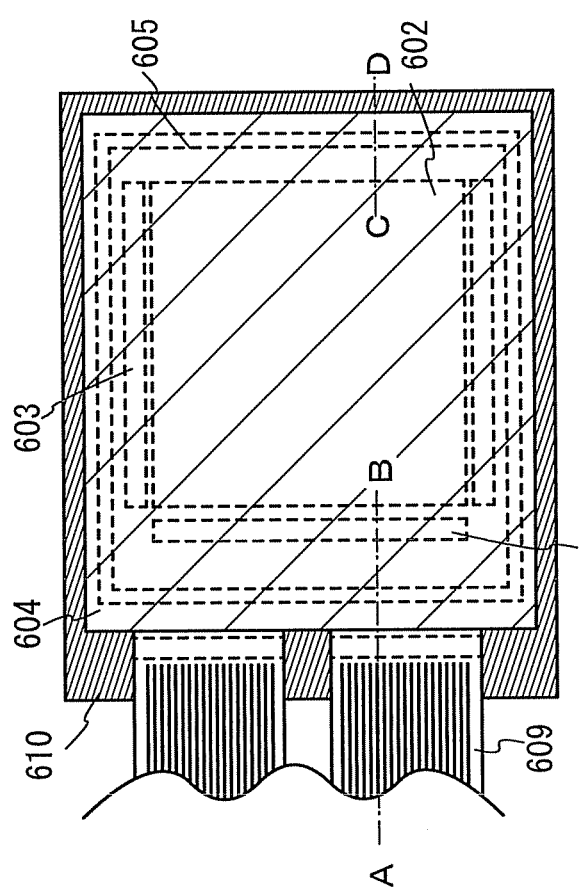
FIGS. 3A and 3B are conceptual diagrams of an active matrix module.
Figure 3B:
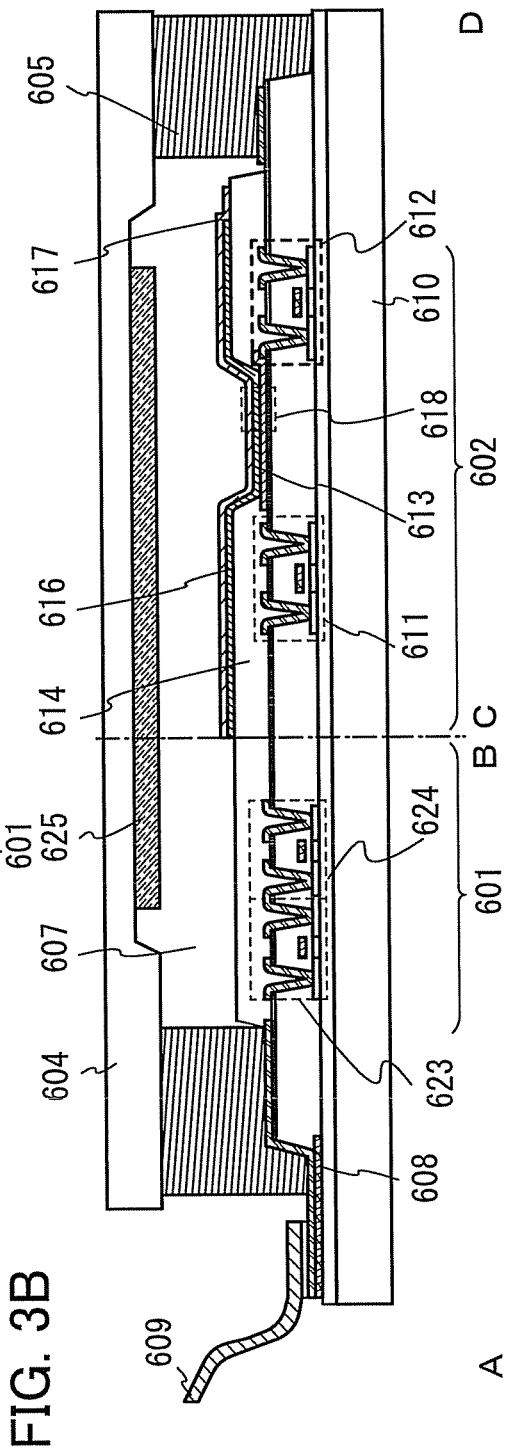

In this embodiment, an example of the display module manufactured using a light-emitting element including any of the bipyridine compounds described in Embodiment 1 will be described with reference to FIGS. 3A and 3B. Note that FIG. 3A is a top view illustrating the display module and FIG. 3B is a cross-sectional view of FIG. 3A taken along A-B and C-D. The display module includes a driver circuit portion (source driver circuit) 601, a pixel portion 602, and a driver circuit portion (gate driver circuit) 603 which are illustrated with dotted lines. These units control light emission of the light-emitting element. Moreover, a reference numeral 604 denotes a sealing substrate; 605, a sealing material; and 607, a space surrounded by the sealing material 605.

Reference numeral 608 denotes a wiring for transmitting signals to be input into the source driver circuit 601 and the gate driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The display module in the present specification includes, in its category, not only the display module itself but also the light-emitting device provided with the FPC or the PWB.

Next, a cross-sectional structure is described with reference to FIG. 3B. The driver circuit portion and the pixel portion are formed over an element substrate 610; the source driver circuit 601, which is a driver circuit portion, and one of the pixels in the pixel portion 602 are illustrated here.

In the source driver circuit 601, a CMOS circuit in which an n-channel TFT 623 and a p-channel TFT 624 are combined is formed. Such a driver circuit may be limited using a variety of circuits such as a CMOS circuit, a PMOS circuit, or an NMOS circuit. Although a driver-integrated type in which the driver circuit is formed over the substrate is described in this embodiment, the present invention is not limited to this type and the driver circuit can be formed outside the substrate.

The pixel portion 602 includes a plurality of pixels each including a switching TFT 611, a current controlling TFT 612, and a first electrode 613 electrically connected to a drain of the current controlling TFT 612. Note that an insulator 614 is formed to cover an edge portion of the first electrode 613. In this embodiment, the insulator 614 is formed using a positive photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 µm to 3 µm. The insulator 614 can be formed using either a negative type photosensitive resin or a positive type photosensitive resin.

A layer 616 containing an organic compound and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like is suitable. Such a stacked structure achieves low wiring resistance, a favorable ohmic contact, and a function as an anode.

In addition, the layer 616 containing an organic compound is formed by any of a variety of methods such as an evaporation method using an evaporation mask, an inkjet method, and a spin coating method. The layer 616 containing an organic compound contains any of the bipyridine compounds described in Embodiment 1. Furthermore, the layer 616 containing an organic compound may be formed using another material such as a low molecular compound or a high molecular compound (e.g., an oligomer or a dendrimer).

As a material used for the second electrode 617, which is formed over the layer 616 containing an organic compound and functions as a cathode, a material having a low work function (e.g., Al, Mg, Li, Ca, or an alloy or compound thereof, such as MgAg, MgIn, or AlLi) is preferably used. In the case where light generated in the layer 616 containing an organic compound passes through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the layer 616 containing an organic compound, and the second electrode 617. The light-emitting element has the structure described in Embodiment 3 or 4. In the display module of this embodiment, the pixel portion, which includes a plurality of light-emitting elements, may include both the light-emitting element with the structure described in Embodiment 3 or 4 and a light-emitting element with a structure other than those.

Furthermore, the sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with filler, and may be filled with an inert gas (e.g., nitrogen or argon), or the sealing material 605.

An epoxy-based resin is preferably used for the sealing material 605. It is preferable that such a material do not transmit moisture or oxygen as much as possible. As the sealing substrate 604, a glass substrate, a quartz substrate, or a plastic substrate formed of fiberglass reinforced plastic (FRP), polyvinyl fluoride (PVF), polyester, acrylic, or the like can be used.

As described above, the display module manufactured using the light-emitting element including any of the bipyridine compounds described in Embodiment 1 can be obtained.

The display module of this embodiment is manufactured using the light-emitting element including any of the bipyridine compounds described in Embodiment 1 and thus can have good characteristics. Specifically, since the bipyridine compounds described in Embodiment 1 each have a wide energy gap and a high triplet excitation level and can prevent energy transfer from a light-emitting substance, a light-emitting element having high emission efficiency can be provided; thus, a display module having reduced power consumption can be provided. In addition, a light-emitting element driven at low voltage can be provided; thus, a display module driven at low voltage can be provided.

Figure 4A:
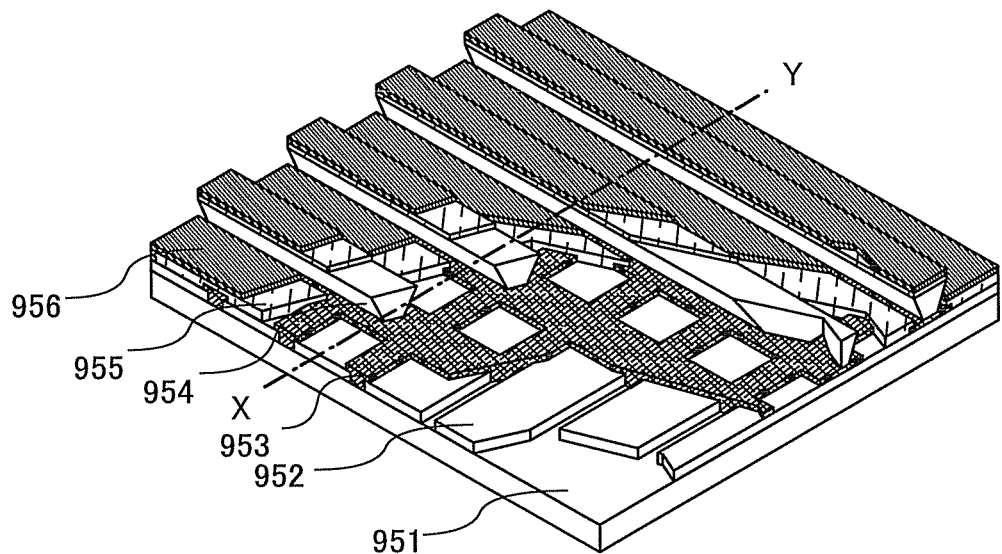
FIGS. 4A and 4B are conceptual diagrams of a passive matrix module.
Figure 4B:
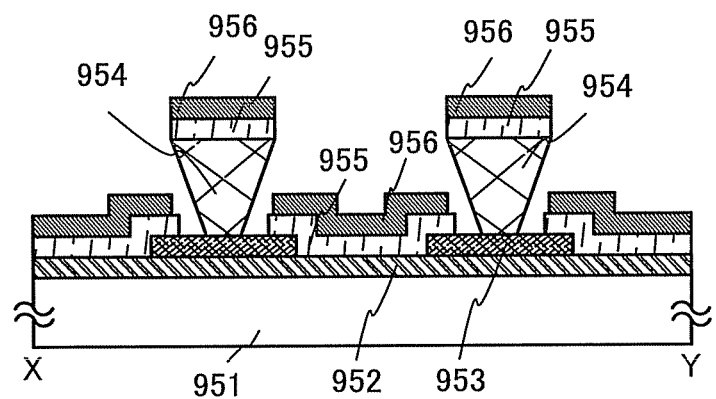

An active matrix display module is described above, whereas a passive matrix display module is described below. FIGS. 4A and 4B illustrate a passive matrix display module manufactured according to the present invention. FIG. 4A is a perspective view of the light-emitting device, and FIG. 4B is a cross-sectional view of FIG. 4A taken along X-Y. In FIGS. 4A and 4B, over a substrate 951, a layer 955 containing an organic compound is provided between an electrode 952 and an electrode 956. An edge portion of the electrode 952 is covered with an insulating layer 953. A partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the base (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition layer 954 in such a manner, a defect of the light-emitting element due to static electricity or the like can be prevented. The passive matrix light-emitting device can also be driven while power consumption is kept low, by including the light-emitting element described in Embodiment 3 or 4 which includes any of the bipyridine compounds described in Embodiment 1 and is capable of operating at low voltage. In addition, the light-emitting device can be driven with less power consumption by including the light-emitting element described in Embodiment 3 or 4 which includes any of the bipyridine compounds described in Embodiment 1 and therefore has high emission efficiency.

A light-emitting device, a display device, and an electronic device can be obtained by combining the display module described in this embodiment with another component.

Since many minute light-emitting elements arranged in a matrix in the display module described above can each be controlled, the display module can be suitably used as a display device for displaying images.

Note that the display module with the above structure can be used as a lighting module. A lighting module with such a structure can change its color variously.

Embodiment 6

Figure 19A:
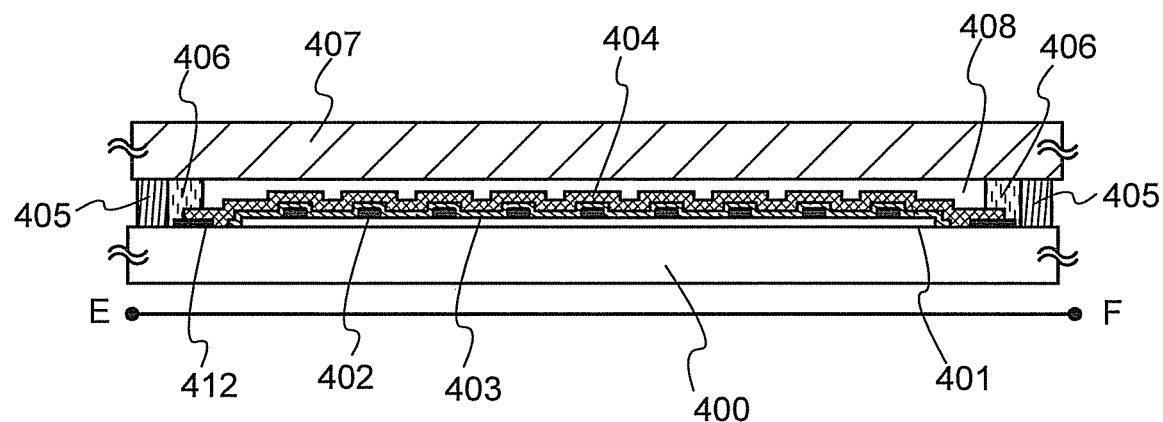
FIGS. 19A and 19B illustrate a lighting module.
Figure 19B:
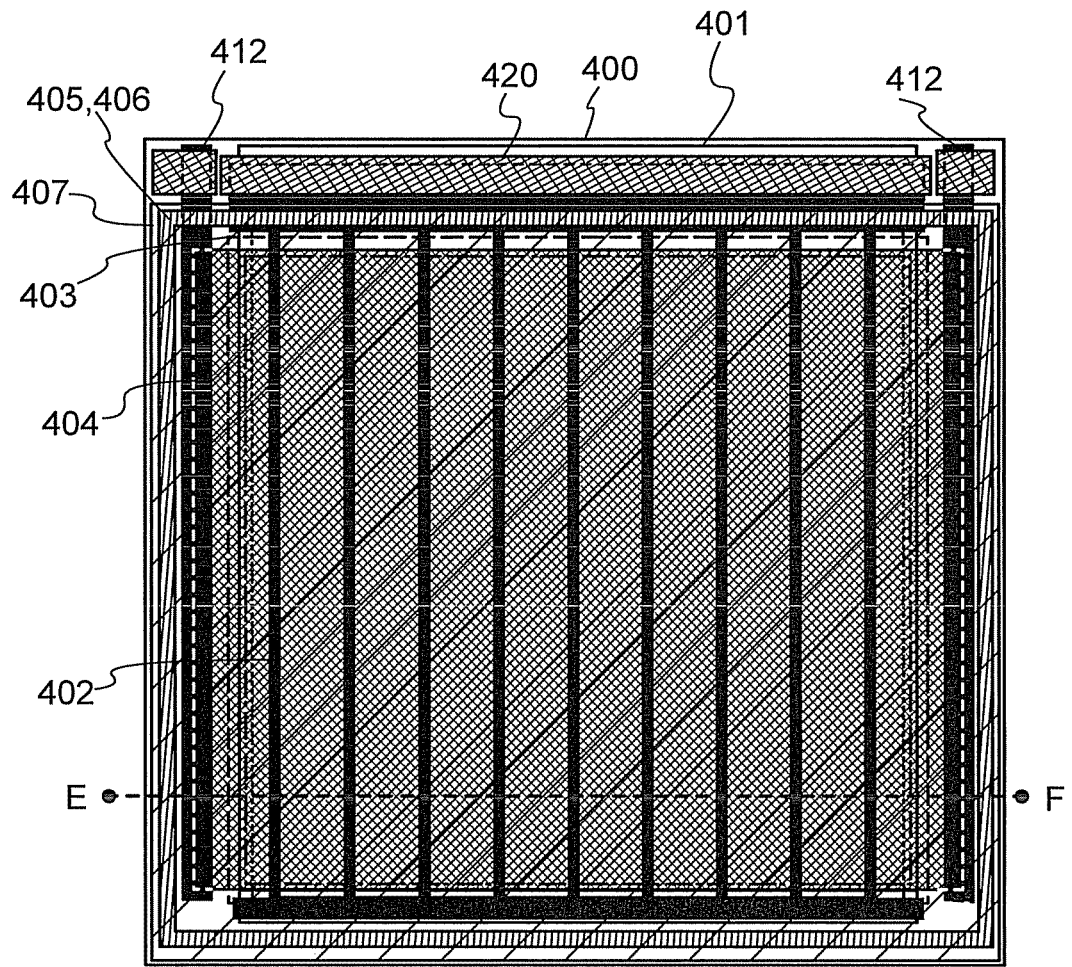

In this embodiment, an example of using a light-emitting element including the bipyridine compound described in Embodiment 1 for a lighting module will be described with reference to FIGS. 19A and 19B. FIG. 19B is a top view of the lighting device, and FIG. 19A is a cross-sectional view taken along E-F in FIG. 19B.

In the lighting module in this embodiment, a first electrode 401 is formed over a substrate 400 which is a support and has a light-transmitting property. The first electrode 401 corresponds to the first electrode 101 in Embodiment 2.

An auxiliary electrode 402 is provided over the first electrode 401. Since light emission is extracted through the first electrode 401 side in the example given in this embodiment, the first electrode 401 is formed using a material having a light-transmitting property. The auxiliary electrode 402 is provided in order to compensate for the low conductivity of the material having a light-transmitting property, and has a function of suppressing luminance unevenness in a light emission surface due to voltage drop caused by the high resistance of the first electrode 401. The auxiliary electrode 402 is formed using a material having at least higher conductivity than the material of the first electrode 401, and is preferably formed using a material having high conductivity such as aluminum. Note that surfaces of the auxiliary electrode 402 other than a portion thereof in contact with the first electrode 401 are preferably covered with an insulating layer. This is for suppressing light emission over the upper portion of the auxiliary electrode 402, which cannot be extracted, for reducing a reactive current, and for suppressing a reduction in power efficiency. Note that a pad 412 for applying a voltage to a second electrode 404 may be formed at the same time as the formation of the auxiliary electrode 402.

A layer 403 containing an organic compound is formed over the first electrode 401 and the auxiliary electrode 402. The layer 403 containing an organic compound corresponds to a structure of the EL layer 103 in Embodiment 3 or 4 or a structure combining the light-emitting units 511 and 512 and the charge generation layer 513. See the explanations of these structures. Note that the layer 403 containing an organic compound is preferably formed to be slightly larger than the first electrode 401 when seen from above, in which case the layer 403 containing an organic compound can also serve as an insulating layer that suppresses a short circuit between the first electrode 401 and the second electrode 404.

The second electrode 404 is formed to cover the layer 403 containing an organic compound. The second electrode 404 corresponds to the second electrode 102 in Embodiment 3 and has a similar structure. In this embodiment, it is preferable that the second electrode 404 be formed using a material having high reflectance because light emission is extracted through the first electrode 401 side. In this embodiment, the second electrode 404 is connected to the pad 412, whereby voltage is applied.

As described above, the lighting module described in this embodiment includes a light-emitting element including the first electrode 401, the layer 403 containing an organic compound, and the second electrode 404 (and the auxiliary electrode 402). Since the light-emitting element is a light-emitting element with high emission efficiency, the lighting module in this embodiment can be a lighting module having low power consumption. Furthermore, since the light-emitting element is a light-emitting element driven at low voltage, the lighting module in this embodiment can be a lighting module having low power consumption. Furthermore, since the light-emitting element is a light-emitting element having high reliability, the lighting module in this embodiment can be a lighting module having high reliability.

The light-emitting element having the above structure is fixed to a sealing substrate 407 with sealing materials 405 and 406 and sealing is performed, whereby the lighting module is completed. Note that a space 408 is surrounded by the sealing materials 405 and 406, the sealing substrate 407, and the substrate 400. It is possible to use only either the sealing material 405 or the sealing material 406. In addition, the inner sealing material 406 can be mixed with a desiccant which enables moisture to be adsorbed, increasing reliability.

When parts of the pad 412, the first electrode 401, and the auxiliary electrode 402 are extended to the outside of the sealing materials 405 and 406, the extended parts can serve as external input terminals. An IC chip 420 mounted with a converter or the like may be provided over the external input terminals.

As described above, since the lighting module described in this embodiment includes a light-emitting element including the bipyridine compound described in Embodiment 1 as an EL element, the lighting module can be a lighting module having low power consumption. Furthermore, the lighting module can be a lighting module driven at low voltage. Furthermore, the lighting module can be a lighting module having high reliability.

By a combination of the lighting module described in this embodiment with another component, a light-emitting device, a lighting device, and an electronic device can be obtained.

Embodiment 7

In this embodiment, a light-emitting device, a display device, a lighting device, and an electronic device, each including the light-emitting element described in Embodiment 3 or 4 will be described. The light-emitting element described in Embodiment 3 or 4 includes any of the bipyridine compounds described in Embodiment 1 and thus has reduced power consumption; as a result, the light-emitting device, the display device, the lighting device, and the electronic devices described in this embodiment can each include a display portion having reduced power consumption. In addition, the light-emitting device, the display device, the lighting device, and the electronic device can have low driving voltage since the light-emitting element described in Embodiment 3 or 4 has low driving voltage.

Examples of the light-emitting device, the display device, the lighting device, and the electronic device to which the above light-emitting element is applied include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, large game machines such as pachinko machines, and the like. Specific examples of these electronic devices are given below.

Figure 5A:
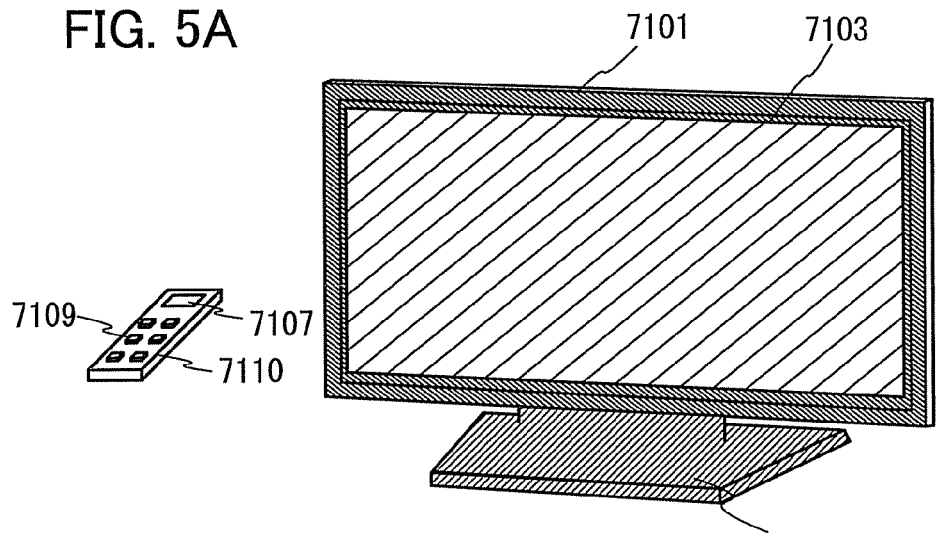
FIGS. 5A to 5D each illustrate an electronic device.

FIG. 5A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as the light-emitting element described in Embodiment 3 or 4 and arranged in a matrix. The light-emitting elements each include any of the bipyridine compounds described in Embodiment 1 and thus can have high emission efficiency and low driving voltage. Therefore, the television device including the display portion 7103 which is formed using the light-emitting elements can have reduced power consumption and low driving voltage.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television set is connected to a communication network with or without wires via the modem, one-way (from a sender to a receiver) or two-way (between a sender and a receiver or between receivers) information communication can be performed.

Figure 5B:
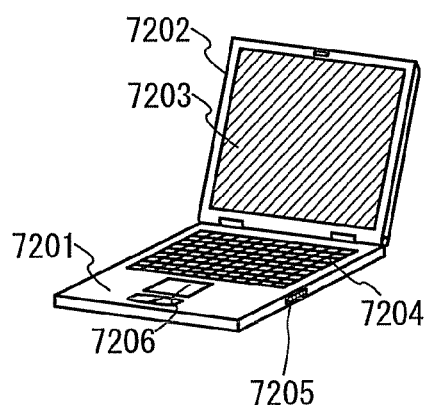

FIG. 5B illustrates a computer, which includes a main body 7201, a housing 7202, a display portion 7203, a keyboard 7204, an external connection port 7205, a pointing device 7206, and the like. Note that this computer is manufactured by using light-emitting elements arranged in a matrix in the display portion 7203, which are the same as that described in Embodiment 3 or 4. The light-emitting elements each include any of the bipyridine compounds described in Embodiment 1 and thus can have high emission efficiency and low driving voltage. Therefore, the computer including the display portion 7203 which is formed using the light-emitting elements can have reduced power consumption and low driving voltage.

Figure 5C:
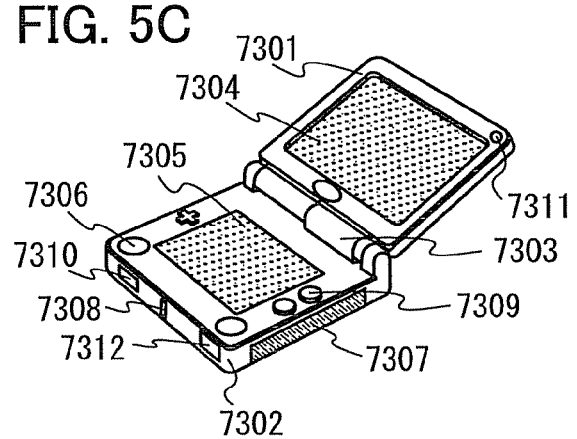

FIG. 5C illustrates a portable game machine having two housings, a housing 7301 and a housing 7302, which are connected with a joint portion 7303 so that the portable game machine can be opened or folded. A display portion 7304 including light-emitting elements which are the same as that described in Embodiment 3 or 4 and arranged in a matrix is incorporated in the housing 7301, and a display portion 7305 is incorporated in the housing 7302. In addition, the portable game machine illustrated in FIG. 5C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as far as the display portion including light-emitting elements which are the same as that described in Embodiment 3 or 4 and arranged in a matrix is used as at least either the display portion 7304 or the display portion 7305, or both, and the structure can include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above. Since the light-emitting elements used in the display portion 7304 have high emission efficiency by including any of the bipyridine compounds described in Embodiment 1, the portable game machine including the above-described display portion 7304 can be a portable game machine having reduced power consumption. Since the light-emitting elements used in the display portion 7304 each have low driving voltage by including any of the bipyridine compounds described in Embodiment 1, the portable game machine can also be a portable game machine driven at low voltage.

Figure 5D:
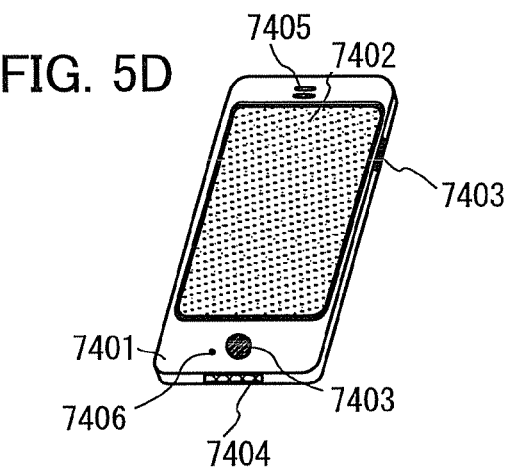

FIG. 5D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone has the display portion 7402 including light-emitting elements which are the same as that described in Embodiment 3 or 4 and arranged in a matrix. The light-emitting elements each include any of the bipyridine compounds described in Embodiment 1 and thus can have high emission efficiency and low driving voltage. Therefore, the mobile phone including the display portion 7402 which is formed using the light-emitting elements can have reduced power consumption and low driving voltage.

When the display portion 7402 of the mobile phone illustrated in FIG. 5D is touched with a finger or the like, data can be input into the mobile phone. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Furthermore, by providing a backlight or a sensing light source which emits a near-infrared light in the display portion, an image of a finger vein, a palm vein, or the like can be taken.

Note that the structure described in this embodiment can be combined with any of the structures described in Embodiments 1 to 5 as appropriate.

As described above, the application range of the light-emitting device having the light-emitting element described in Embodiment 3 or 4 which includes a bipyridine compound described in Embodiment 1 is wide so that this light-emitting device can be applied to electronic devices in a variety of fields. By using any of the bipyridine compounds described in Embodiment 1, an electronic device having reduced power consumption and low driving voltage can be obtained.

The light-emitting element including any of the bipyridine compounds described in Embodiment 1 can also be used for a light source device. One mode of application of the light-emitting element including any of the bipyridine compounds described in Embodiment 1 to a light source device is described with reference to FIG. 6. Note that the light source device includes a light-emitting element including any of the bipyridine compounds described in Embodiment 1 as a light irradiation unit and at least includes an input-output terminal portion which supplies current to the light-emitting element. Furthermore, the light-emitting element is preferably shielded from the outside atmosphere by sealing.

Figure 6:
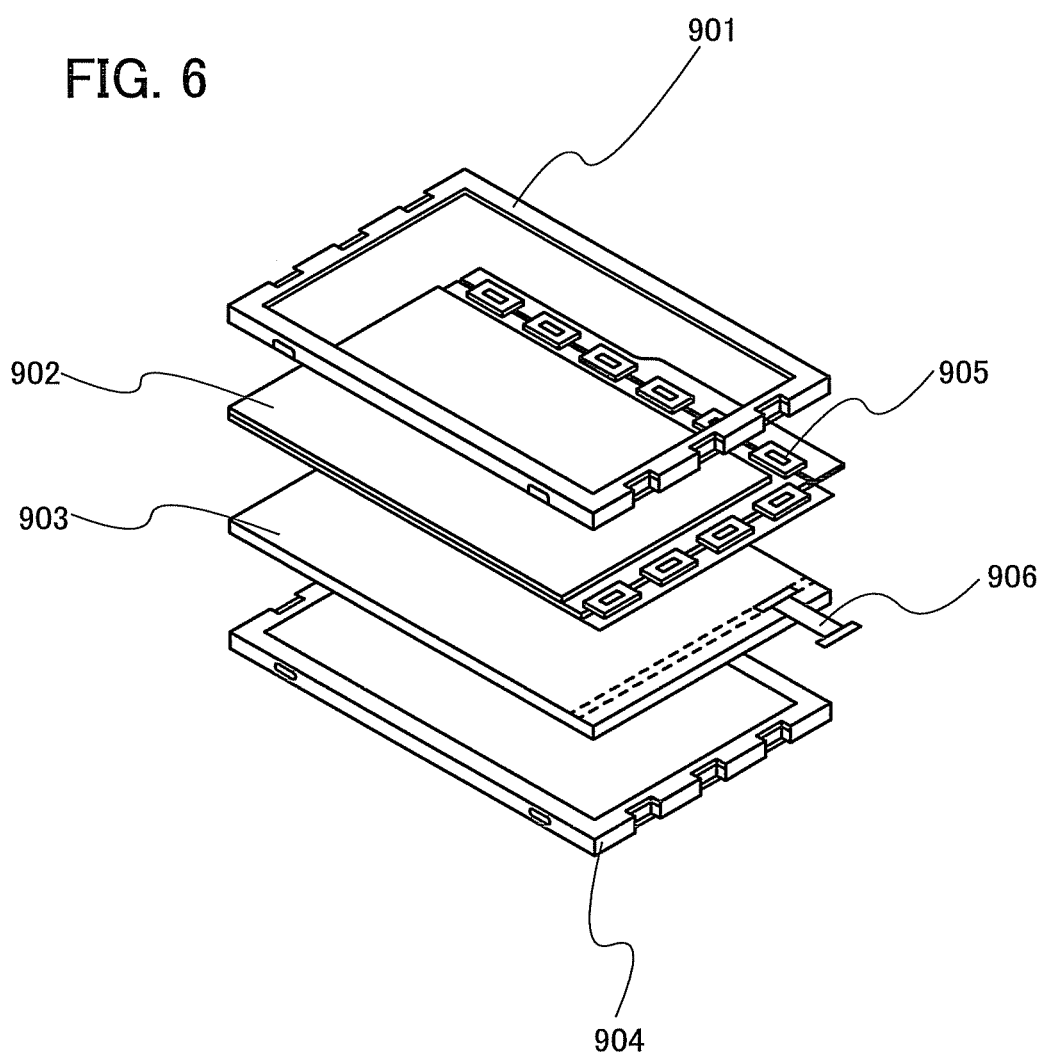
FIG. 6 illustrates a light source device.

FIG. 6 illustrates an example of a liquid crystal display device using the light-emitting elements including any of the bipyridine compounds described in Embodiment 1 for a backlight. The liquid crystal display device illustrated in FIG. 6 includes a housing 901, a liquid crystal layer 902, a backlight 903, and a housing 904. The liquid crystal layer 902 is connected to a driver IC 905. The light-emitting element including any of the bipyridine compounds described in Embodiment 1 is used in the backlight 903, to which current is supplied through a terminal 906.

The light-emitting element including any of the bipyridine compounds described in Embodiment 1 is used for the backlight of the liquid crystal display device; thus, the backlight can have reduced power consumption. In addition, the use of the light-emitting element including any of the bipyridine compounds described in Embodiment 1 enables manufacture of a planar-emission light source device and further a larger-area planar-emission light source device; therefore, the backlight can be a larger-area backlight, and the liquid crystal display device can also be a larger-area device. Furthermore, the backlight using the light-emitting element including any of the bipyridine compounds described in Embodiment 1 can be thinner than a conventional one; accordingly, the display device can also be thinner.

Figure 7:
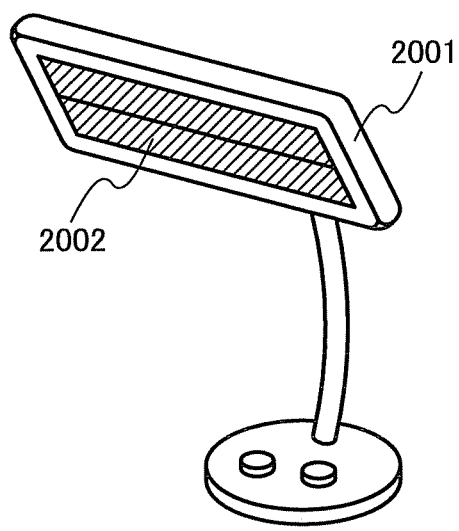
FIG. 7 illustrates a lighting device.

FIG. 7 illustrates an example in which the light-emitting element including any of the bipyridine compounds described in Embodiment 1 is used for a table lamp which is a lighting device. The table lamp illustrated in FIG. 7 includes a housing 2001 and a light source 2002, and the light-emitting element including any of the bipyridine compounds described in Embodiment 1 is used for the light source 2002.

Figure 8:
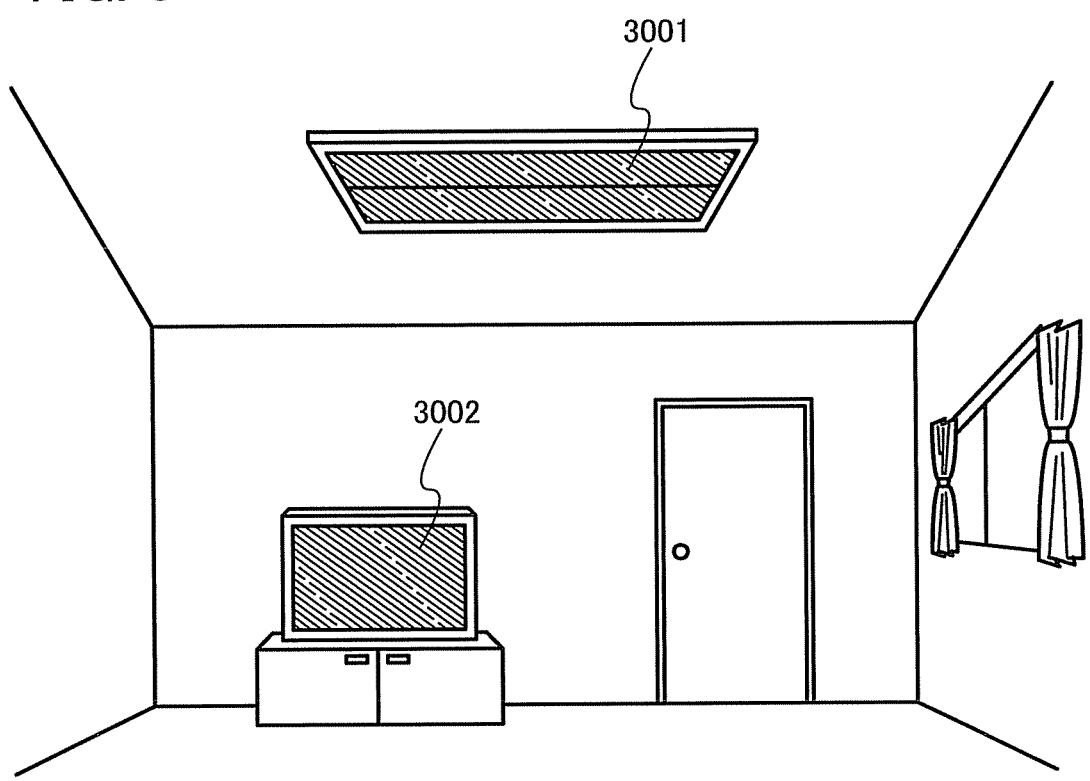
FIG. 8 illustrates a lighting device.

FIG. 8 illustrates an example in which the light-emitting element including any of the bipyridine compounds described in Embodiment 1 is used for an indoor lighting device 3001. Since the light-emitting element including any of the bipyridine compounds described in Embodiment 1 has reduced power consumption, a lighting device that has reduced power consumption can be obtained. Furthermore, since the light-emitting element including any of the bipyridine compounds described in Embodiment 1 can have a large area, the light-emitting element can be used for a large-area lighting device. Furthermore, since the light-emitting element including any of the bipyridine compounds described in Embodiment 1 is thin, a lighting device having a reduced thickness can be manufactured.

Figure 9:
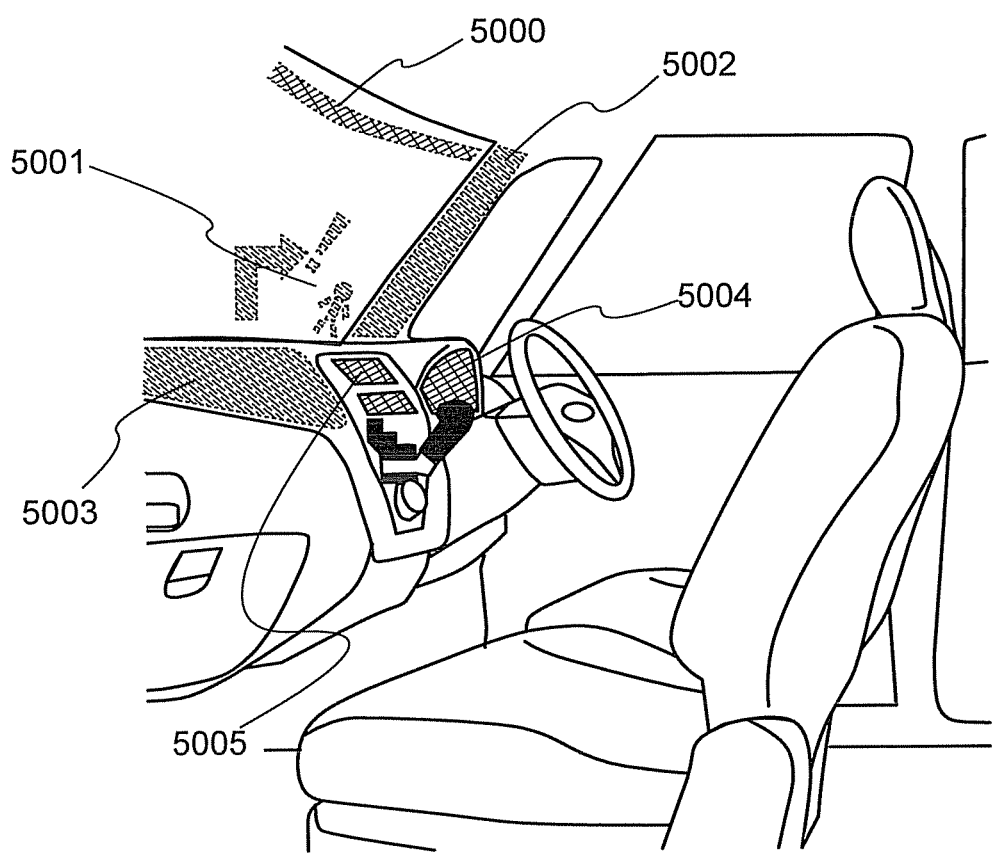
FIG. 9 illustrates in-vehicle display devices and lighting devices.

The light-emitting element including any of the bipyridine compounds described in Embodiment 1 can also be used for an automobile windshield or an automobile dashboard. FIG. 9 illustrates one mode in which the light-emitting elements including any of the bipyridine compounds described in Embodiment 1 are used for an automobile windshield and an automobile dashboard. Display regions 5000 to 5005 each include the light-emitting element including the bipyridine compound described in Embodiment 1.

The display regions 5000 and 5001 are display devices which are provided in the automobile windshield and in which light-emitting elements including any of the bipyridine compounds described in Embodiment 1 are incorporated. The light-emitting element including any of the bipyridine compounds described in Embodiment 1 can be formed into a so-called see-through display device, through which the opposite side can be seen, by including a first electrode and a second electrode formed of electrodes having light-transmitting properties. Such see-through display devices can be provided even in the windshield of the car, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and in which the light-emitting element including a bipyridine compound described in Embodiment 1 is incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

By including any of the bipyridine compounds described in Embodiment 1, the light-emitting element including the bipyridine compound has low driving voltage and lower power consumption. Therefore, load on a battery is small even when a number of large screens such as the display regions 5000 to 5005 are provided, which provides comfortable use. For that reason, the light-emitting device and the lighting device each of which includes the light-emitting element including any of the bipyridine compounds described in Embodiment 1 can be suitably used as an in-vehicle light-emitting device and lighting device.

Figure 10A:
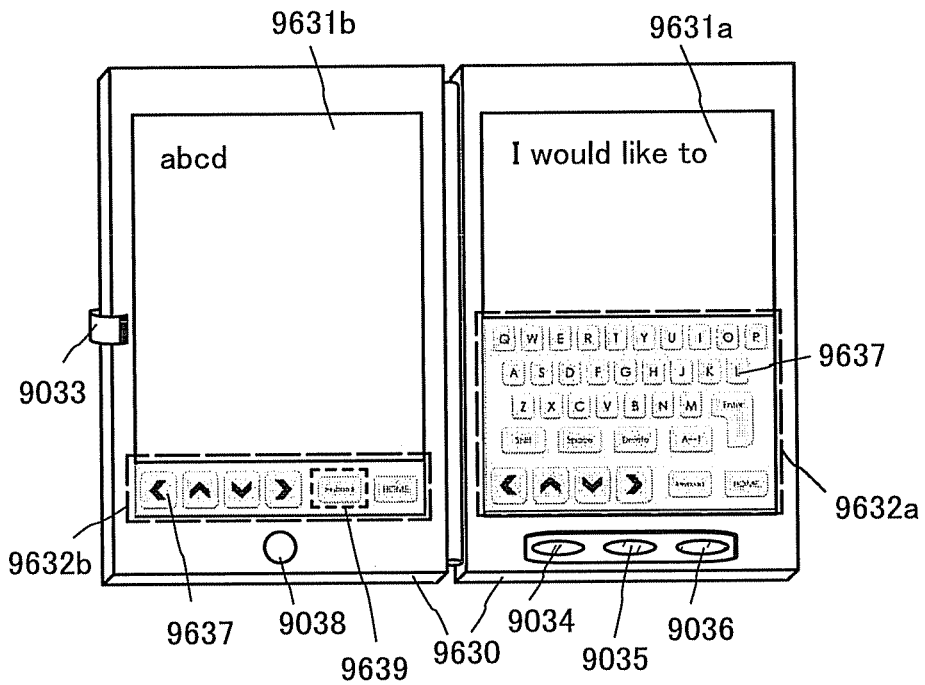
FIGS. 10A to 10C illustrate an electronic device.
Figure 10B:
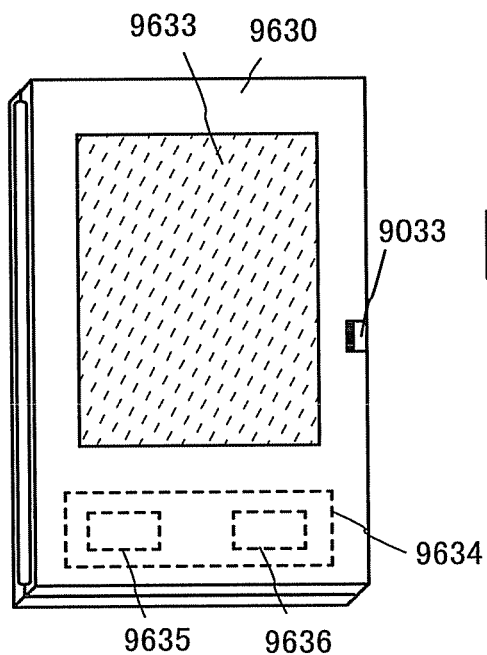

FIGS. 10A and 10B illustrate an example of a foldable tablet. FIG. 10A illustrates the tablet which is unfolded. The tablet includes a housing 9630, a display portion 9631*a*, a display portion 9631*b*, a display mode switch 9034, a power switch 9035, a power-saving mode switch 9036, a clasp 9033, and an operation switch 9038. Note that in the tablet, one or both of the display portion 9631*a* and the display portion 9631*b* is/are formed using a light-emitting device which includes a light-emitting element including any of the bipyridine compounds described in Embodiment 1.

Part of the display portion 9631*a* can be a touchscreen region 9632*a* and data can be input when a displayed operation key 9637 is touched. Although half of the display portion 9631*a* has only a display function and the other half has a touchscreen function, one embodiment of the present invention is not limited to the structure. The whole display portion 9631*a* may have a touchscreen function. For example, a keyboard is displayed on the entire region of the display portion 9631*a* so that the display portion 9631*a* is used as a touchscreen; thus, the display portion 9631*b* can be used as a display screen.

Like the display portion 9631*a*, part of the display portion 9631*b* can be a touchscreen region 9632*b*. When a switching button 9639 for showing/hiding a keyboard on the touchscreen is touched with a finger, a stylus, or the like, the keyboard can be displayed on the display portion 9631*b*.

Touch input can be performed in the touchscreen region 9632*a* and the touchscreen region 9632*b* at the same time.

The display mode switch 9034 can switch the display between portrait mode, landscape mode, and the like, and between monochrome display and color display, for example. The power-saving switch 9036 can control display luminance in accordance with the amount of external light in use of the tablet detected by an optical sensor incorporated in the tablet. Another detection device including a sensor for detecting inclination, such as a gyroscope or an acceleration sensor, may be incorporated in the tablet, in addition to the optical sensor.

Although FIG. 10A illustrates an example in which the display portion 9631*a* and the display portion 9631*b* have the same display area, one embodiment of the present invention is not limited to the example. The display portion 9631*a* and the display portion 9631*b* may have different display areas and different display quality. For example, one display panel may be capable of higher-definition display than the other display panel.

FIG. 10B illustrates the tablet which is folded. The tablet includes the housing 9630, a solar cell 9633, a charge and discharge control circuit 9634, a battery 9635, and a DC-to-DC converter 9636. As an example, FIG. 10B illustrates the charge and discharge control circuit 9634 including the battery 9635 and the DC-to-DC converter 9636.

Since the tablet is foldable, the housing 9630 can be closed when the tablet is not in use. As a result, the display portion 9631*a* and the display portion 9631*b* can be protected, thereby providing a tablet with high endurance and high reliability for long-term use.

The tablet illustrated in FIGS. 10A and 10B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet can supply power to the touchscreen, the display portion, a video signal processing portion, or the like. Note that the solar cell 9633 is preferably provided on one or two surfaces of the housing 9630, in which case the battery 9635 can be charged efficiently.

Figure 10C:
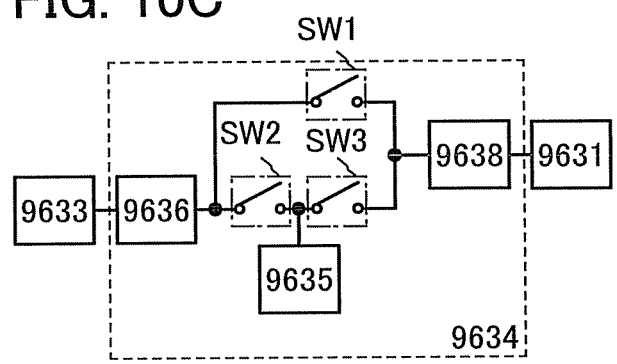

The structure and operation of the charge and discharge control circuit 9634 illustrated in FIG. 10B will be described with reference to a block diagram of FIG. 10C. FIG. 10C illustrates the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 illustrated in FIG. 10B.

First, description is made on an example of the operation in the case where power is generated by the solar cell 9633 with the use of external light. The voltage of the power generated by the solar cell is raised or lowered by the DC-to-DC converter 9636 so as to be voltage for charging the battery 9635. Then, when power supplied from the battery 9635 charged by the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module which is capable of charging by transmitting and receiving power by wireless (without contact), or another charge means used in combination, and the power generation means is not necessarily provided.

Needless to say, one embodiment of the present invention is not limited to the electronic device having the shape illustrated in FIGS. 10A to 10C as long as the display portion 9631 is included.

Example 1

In this example, a method for synthesizing 5,6-bis[4-(10-phenyl-9-anthryl)phenyl]-2,2'-bipyridine (abbreviation: PAP2BPy) that is the bipyridine compound described in Embodiment 1 will be described.

Synthesis Example 1

Synthesis of 5,6-bis[4-(10-phenyl-9-anthryl)phenyl]-2,2'-bipyridine (abbreviation: PAP2BPy)

In a 100-mL three-neck flask were put 0.74 g (1.6 mmol) of 5,6-bis(4-bromophenyl)-2,2'-bipyridine, 1.1 g (3.7 mmol) of 10-phenylanthracene-9-boronic acid, 0.79 g (7.4 mmol) of sodium carbonate, 20 mL of toluene, 5 mL of ethanol, and 5 mL of water. The mixture was degassed by being stirred under reduced pressure, and the air in the flask was replaced with nitrogen. To this mixture was added 74 mg (0.14 mmol) of tetrakis(triphenylphosphine)palladium(0), and the mixture was refluxed at 120° C. under a nitrogen stream for ten hours. After a predetermined time, water was added to this mixture to separate an aqueous layer and an organic layer, and then an organic substance was extracted with toluene from the aqueous layer. The obtained extracted solution and the organic layer were combined and washed with saturated saline, the aqueous layer and the organic layer are separated, and the organic layer was dried with magnesium sulfate. The mixture was gravity filtered, and the obtained filtrate was concentrated to give an oily substance. The obtained oily substance was purified by silica gel column chromatography (toluene), so that a solid was obtained. A methanol suspension of the obtained solid was irradiated with ultrasonic waves, and a solid was collected by suction filtration. The obtained solid was recrystallized with toluene to give 0.56 g of light yellow powder, which was the objective substance, in a yield of 43%. The synthesis scheme of this reaction is shown below.

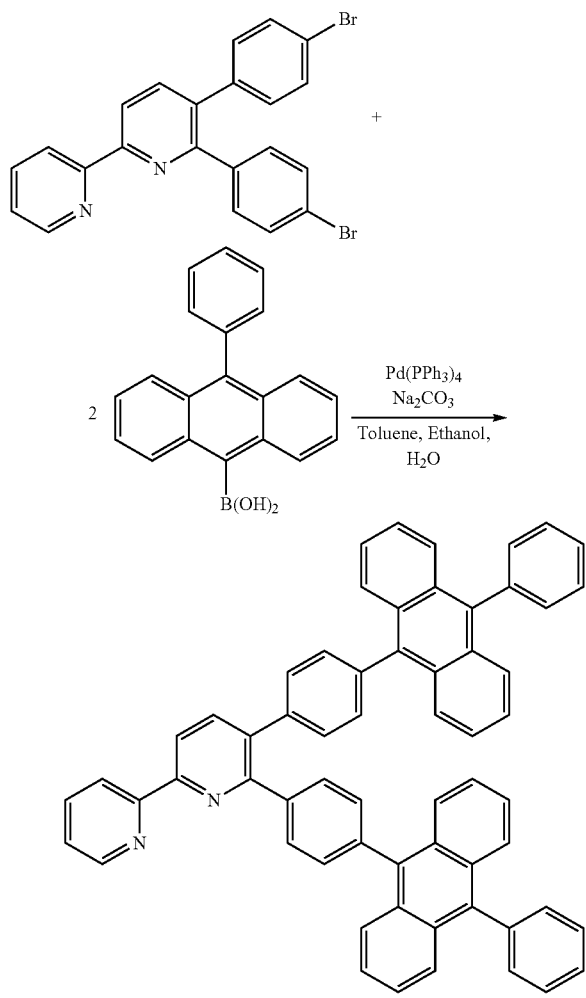

Then, 0.56 g of the obtained light yellow powder was purified by a train sublimation method. The sublimation purification conditions were as follows: the pressure was 10 Pa, the flow rate of argon gas was 5 mL/min, and the temperature was 330° C. After the sublimation purification, 0.45 g of yellow powder was obtained in a collection rate of 80%.

The yellow powder was subjected to nuclear magnetic resonance (NMR) spectroscopy. The measurement data are shown below.

$^1$H NMR (CD$_2$Cl$_2$, 300 MHz): δ=7.15-7.30 (m, 8H), 7.39-7.43 (m, 1H), 7.46-7.68 (m, 20H), 7.77 (t, J=8.4 Hz, 4H), 7.88-7.96 (m, 3H), 8.20 (d, J=8.4 Hz, 1H), 8.65 (d, J=7.8 Hz, 1H), 8.73 (d, J=8.4 Hz, 1H), 8.76-8.78 (m, 1H)

Figure 11A:
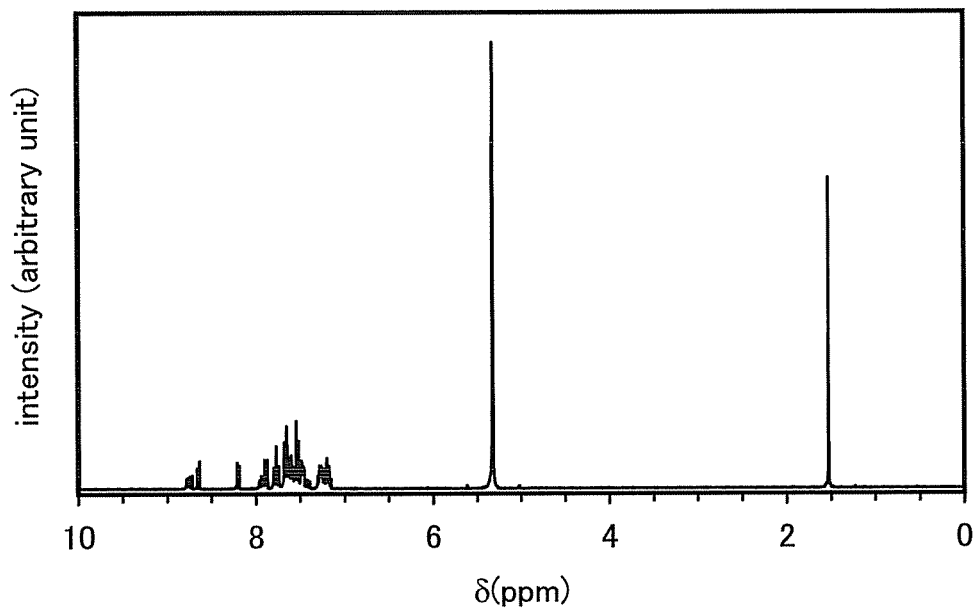
FIGS. 11A and 11B are NMR charts of PAP2BPy.
Figure 11B:
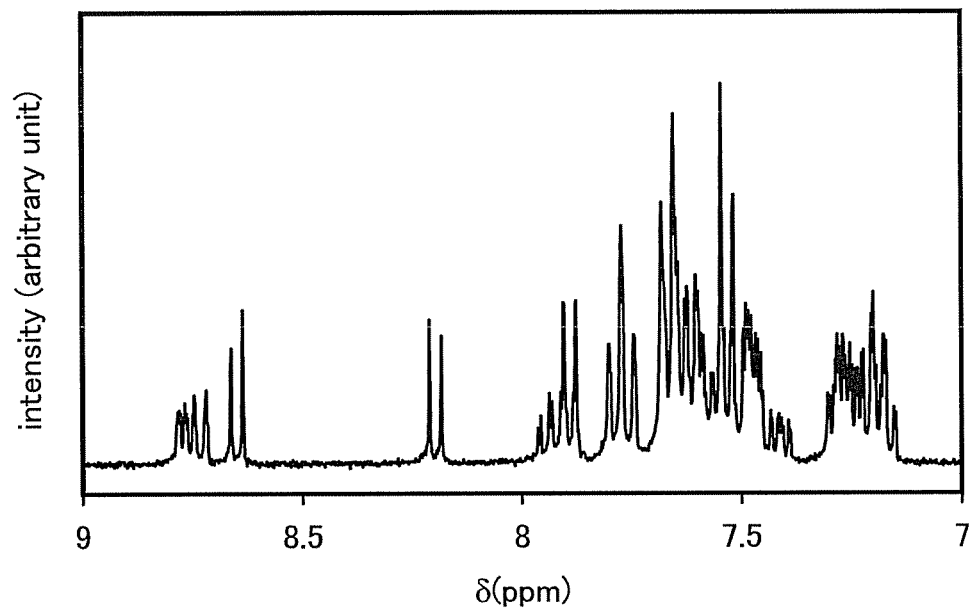

FIGS. 11A and 11B each show a $^1$H NMR chart. Note that FIG. 11B is an enlarged chart of FIG. 11A. The measurement results demonstrate that the objective substance 5,6-bis[4-(10-phenyl-9-anthryl)phenyl]-2,2'-bipyridine (abbreviation: PAP2BPy) was able to be obtained.

A thermogravimetry-differential thermal analysis (TG-DTA) of the obtained PAP2BPy was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) at normal pressure at a temperature rising rate of 10° C./min. The relationship between weight and temperature (thermogravimetry) demonstrates that the 5% weight loss temperature was 500° C. or higher and the melting point was 327° C. Thus, PAP2BPy was indicative of high heat resistance.

Figure 12A:
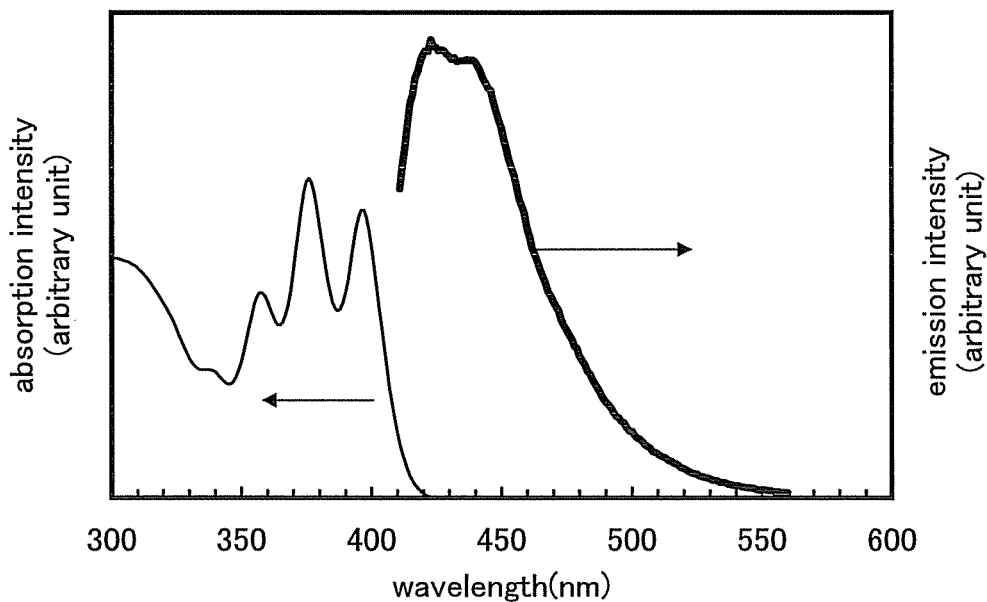
FIGS. 12A and 12B each show an absorption and emission spectra of PAP2BPy.
Figure 12B:
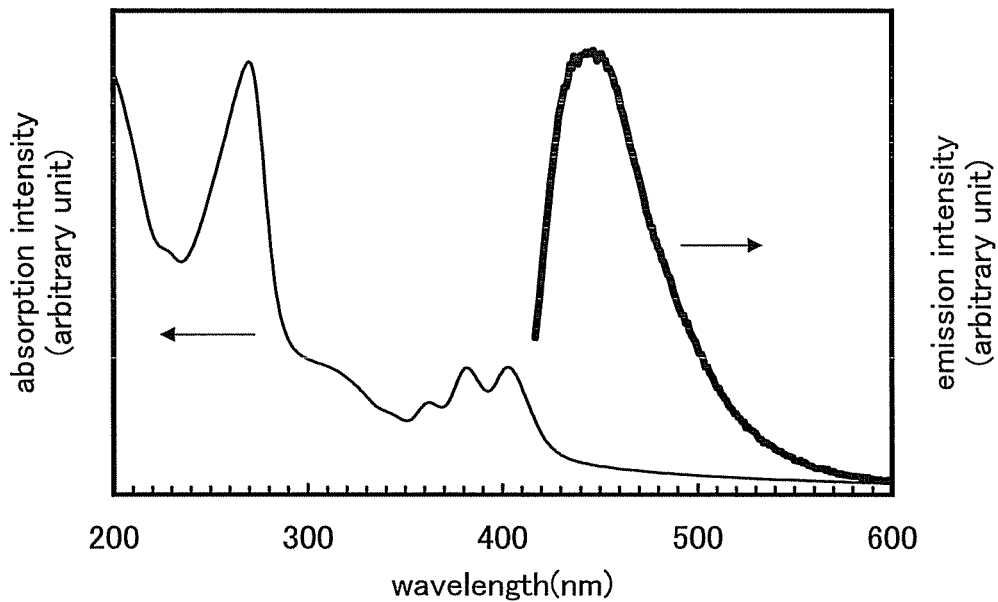

FIG. 12A shows an absorption spectrum and an emission spectrum of PAP2BPy in a toluene solution of PAP2BPy, and FIG. 12B shows an absorption spectrum and an emission spectrum of a thin film of PAP2BPy. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of PAP2BPy in the toluene solution of PAP2BPy was obtained by subtracting the absorption spectra of quartz and toluene from the absorption spectra of quartz and the solution, and the absorption spectrum of the thin film was obtained by subtracting the absorption spectrum of the quartz substrate from the absorption spectra of the quartz substrate and the thin film. In FIGS. 12A and 12B, the horizontal axis indicates the wavelength (nm) and the vertical axis indicates the intensity (arbitrary unit). In the case of the toluene solution, absorption peaks were observed at around 397 nm, 376 nm, and 358 nm, and an emission wavelength peak was observed at 423 nm (at an excitation wavelength of 394 nm). In the case of the thin film, absorption peaks were observed at around 403 nm, 382 nm, 362 nm, 317 nm, and 270 nm, and an emission wavelength peak was observed at 445 nm (at an excitation wavelength of 401 nm).

Furthermore, the ionization potential of PAP2BPy in a thin film state was measured by a photoelectron spectrometer (AC-2, produced by Riken Keiki, Co., Ltd.) in the atmosphere. The obtained value of the ionization potential was converted into a negative value to give a HOMO level of PAP2BPy of −5.83 eV. From the data of the absorption spectrum of the thin film in FIG. 12B, the absorption edge of PAP2BPy, which was obtained from a Tauc plot with an assumption of direct transition, was 2.94 eV. Therefore, the optical energy gap of PAP2BPy in a solid state can be estimated at 2.94 eV; from the values of the HOMO level obtained above and this energy gap, the LUMO level of PAP2BPy can be estimated at −2.89 eV. This reveals that PAP2BPy in the solid state has an energy gap as wide as 2.64 eV.

Electrochemical characteristics (oxidation and reduction characteristics) of a solution of PAP2BPy were measured by cyclic voltammetry (CV). Note that an electrochemical analyzer (ALS model 600A or 600C, produced by BAS Inc.) was used for the measurements.

In the measurements, the potential of a working electrode with respect to the reference electrode was changed within an appropriate range, so that the oxidation peak potential and the reduction peak potential were each obtained. From the obtained peak potentials, the HOMO and LUMO levels of PAP2BPy were respectively calculated at −5.78 eV and −2.70 eV.

The calculations of the HOMO and LUMO levels using CV measurement are detailed below.

For a solution for the CV measurements, dehydrated N,N-dimethylformamide (DMF, produced by Sigma-Aldrich Inc., 99.8%, catalog No. 22705-6) was used as a solvent, and tetra-n-butylammonium perchlorate (n-Bu$_4$NClO$_4$, produced by Tokyo Chemical Industry Co., Ltd., catalog No. T0836), which was a supporting electrolyte, was dissolved in the solvent such that the concentration thereof was 100 mmol/L. Furthermore, the object to be measured was also dissolved in the solvent such that the concentration thereof was 2 mmol/L.

A platinum electrode (a PTE platinum electrode, produced by BAS Inc.) was used as the working electrode; a platinum electrode (a VC-3 Pt counter electrode (5 cm), produced by BAS Inc.) was used as an auxiliary electrode; and an Ag/Ag$^+$ electrode (an RE5 nonaqueous solvent reference electrode, produced by BAS Inc.) was used as the reference electrode. Note that the measurements were conducted at room temperature (20° C. to 25° C.). The scan rates for the CV measurements were uniformly set to 0.1 V/s.

In the measurement of the oxidation characteristics, one cycle was scanning in which the potential of the working electrode with respect to the reference electrode was changed from −0.28 V to 1.10 V and then changed from 1.10 V to −0.28 V.

In the measurements of the reduction characteristics, one cycle was scanning in which the potential of the working electrode with respect to the reference electrode was changed from −1.14 V to −2.40 V and then changed from −2.40 V to −1.14 V.

The HOMO level was obtained by subtraction of a half-wave potential $E_{1/2}$ (an intermediate potential between $E_{pa}$ and $E_{pc}$), which was calculated from the oxidation peak potential $E_{pa}$ and the reduction peak potential $E_{pc}$ obtained in the measurement of the oxidation characteristics of PAP2BPy, from the potential energy of the reference electrode, which was used, with respect to the vacuum level.

The oxidation peak potential $E_{pa}$ was 0.91 V and the reduction peak potential $E_{pc}$ was 0.76 V according to the measurement of the oxidation characteristics of PAP2BPy. The half-wave potential $E_{1/2}$ was therefore 0.84 V, and since the potential energy of the reference electrode, which was used in the measurements, with respect to the vacuum level is −4.94 eV, the HOMO level of the solution of PAP2BPy can be calculated as follows: −4.94−0.84=−5.78 eV.

The LUMO level was obtained by subtraction of a half-wave potential $E_{1/2}$ (an intermediate potential between $E_{pa}$ and $E_{pc}$), which was calculated from the reduction peak potential $E_{pc}$ and the oxidation peak potential $E_{pa}$ obtained in the measurement of the reduction characteristics of PAP2BPy, from the potential energy of the reference electrode, which was used, with respect to the vacuum level.

The reduction peak potential $E_{pc}$ was −2.29 V and the oxidation peak potential $E_{pa}$ was −2.19 V according to the measurement of the reduction characteristics of PAP2BPy. The half-wave potential $E_{1/2}$ was therefore −2.24 V, and since the potential energy of the reference electrode, which was used in the measurements, with respect to the vacuum level is −4.94 eV, the LUMO level of the solution of PAP2BPy can be calculated as follows: −4.94−(−2.24)=−2.70 eV.

Note that the potential energy of the reference electrode (Ag/Ag$^+$ electrode) with respect to the vacuum level corresponds to the Fermi level of the Ag/Ag$^+$ electrode, and should be calculated from a value obtained by measuring a substance whose potential energy with respect to the vacuum level is known, with the use of the reference electrode (Ag/Ag$^+$ electrode).

How the potential energy (eV) of the reference electrode (Ag/Ag$^+$ electrode), which was used in this example, with respect to the vacuum level is calculated will be specifically described. It is known that the oxidation-reduction potential of ferrocene in methanol is +0.610 V [vs. SHE] with respect to the standard hydrogen electrode (reference: Christian R. Goldsmith et al., *J. Am. Chem. Soc.*, Vol. 124, No. 1, pp. 83-96, 2002). In contrast, using the reference electrode used in this example, the oxidation-reduction potential of ferrocene in methanol was calculated at +0.11 V [vs. Ag/Ag$^+$]. Thus, it was found that the potential energy of this reference electrode was lower than that of the standard hydrogen electrode by 0.50 [eV].

Here, it is known that the potential energy of the standard hydrogen electrode with respect to the vacuum level is −4.44 eV (reference: Toshihiro Ohnishi and Tamami Koyama, *High molecular EL material*, Kyoritsu shuppan, pp. 64-67). Therefore, the potential energy of the reference electrode, which was used in this example, with respect to the vacuum level can be calculated as follows: −4.44−0.50=−4.94 [eV].

Example 2

In this example, a method for synthesizing 5,6-bis[4'-(10-phenyl-9-anthryl)biphenyl-4-yl]-2,2'-bipyridine (abbreviation: PAPP2BPy) that is the bipyridine compound described in Embodiment 1 will be described.

Synthesis Example 2

Synthesis of 5,6-bis[4'-(10-phenyl-9-anthryl)biphenyl-4-yl]-2,2'-bipyridine

In a 50-mL three-neck flask were put 0.70 g (1.5 mmol) of 5,6-bis(4-bromophenyl)-2,2'-bipyridine, 1.2 g (3.3 mmol) of 4-(10-phenyl-9-anthryl)phenyl boronic acid, 0.79 g (7.5 mmol) of sodium carbonate, 15 mL of toluene, 5 mL of ethanol, and 5 mL of water. The mixture was degassed by being stirred under reduced pressure, and the air in the flask was replaced with nitrogen. To this mixture was added 80 mg (69 μmol) of tetrakis(triphenylphosphine)palladium(0), and the mixture was refluxed at 120° C. under a nitrogen stream for six hours. After a predetermined time, the mixture was cooled to room temperature, and the precipitated solid was collected by suction filtration. The obtained solid was dissolved in chloroform and washed with water and saturated saline in this order, and the organic layer was dried with magnesium sulfate. The obtained mixture was gravity filtered, and the obtained filtrate was concentrated to give a solid. A methanol suspension of the obtained solid was irradiated with ultrasonic waves, and a solid was collected by suction filtration. The obtained solid was recrystallized with toluene to give 1.2 g of light yellow powder in a yield of 84%. The synthesis scheme of this reaction is shown below.

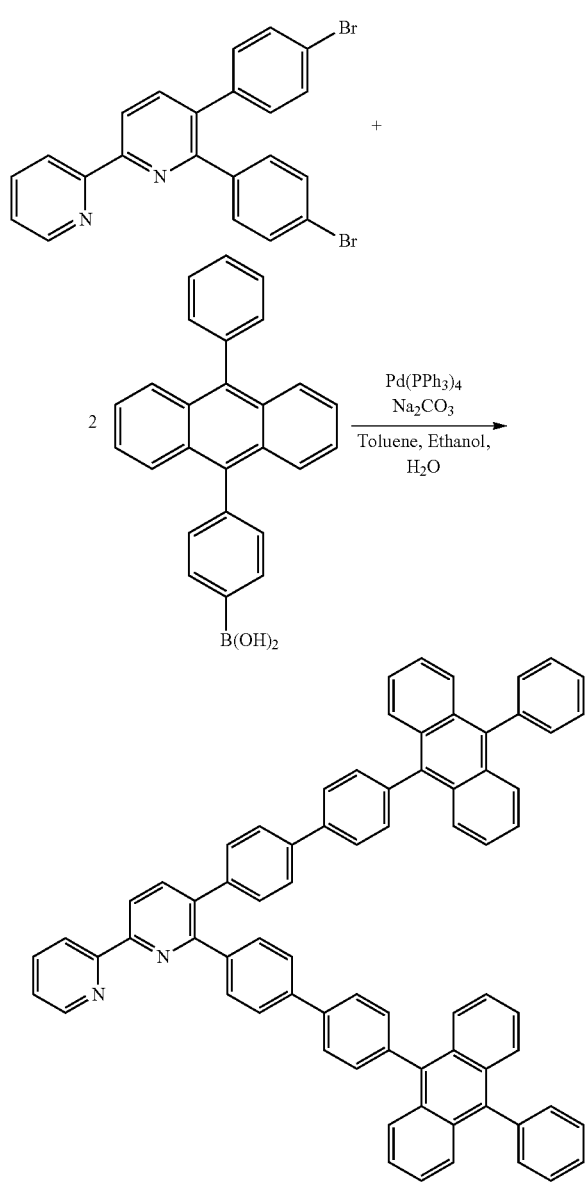

The light yellow powder was subjected to nuclear magnetic resonance (NMR) spectroscopy. The measurement data are shown below.

$^1$H NMR (CDCl$_3$, 300 MHz): δ=7.29-7.37 (m, 9H), 7.46-7.63 (m, 16H), 7.68-7.80 (m, 14H), 7.84-7.90 (m, 5H), 8.00 (d, J=7.8 Hz, 1H), 8.53 (d, J=8.4 Hz, 1H), 8.69 (d, J=7.8 Hz, 1H), 8.75 (dd, J=3.9 Hz, 1.2 Hz, 1H)

Figure 13A:
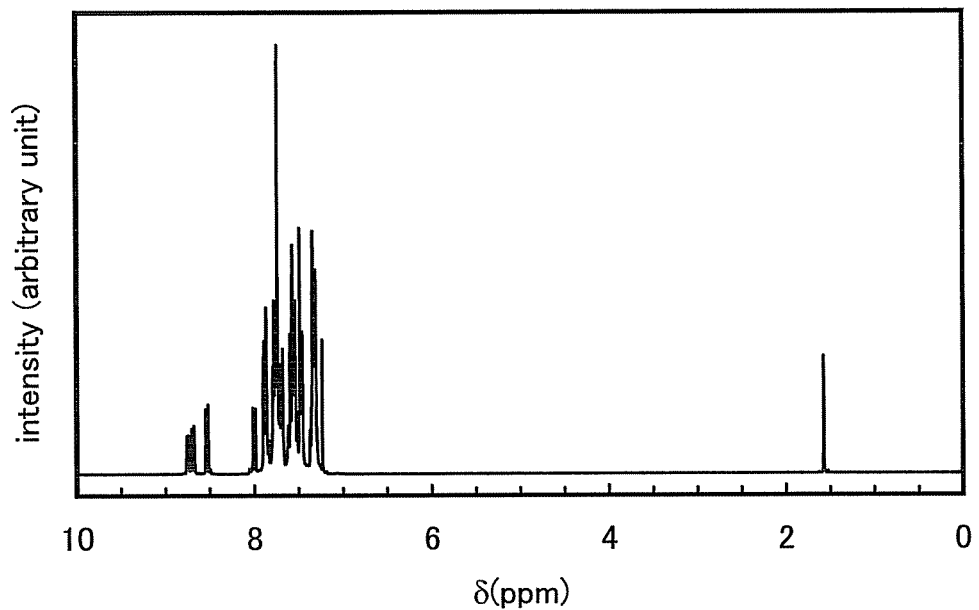
FIGS. 13A and 13B are NMR charts of PAPP2BPy.
Figure 13B:
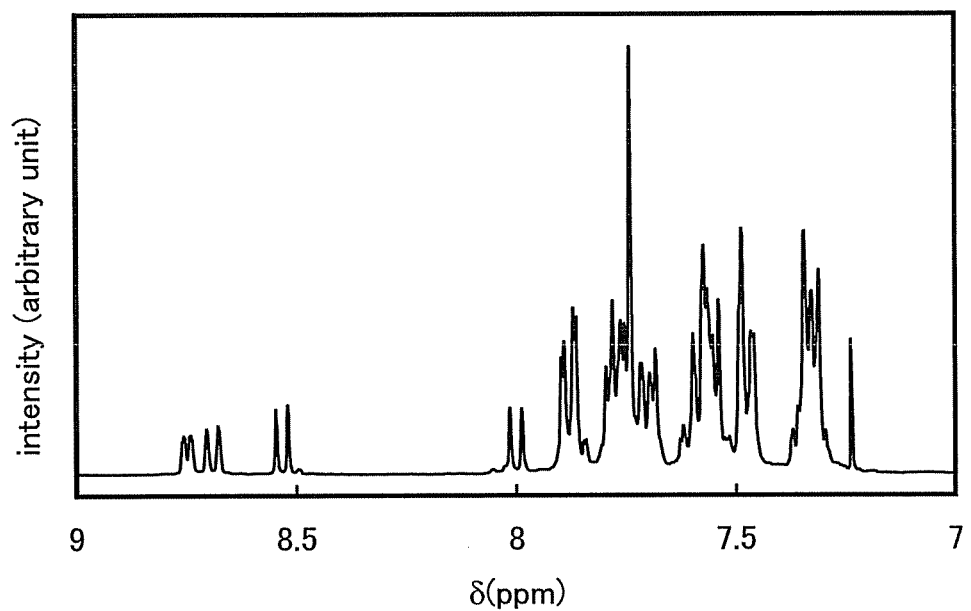

FIGS. 13A and 13B each show a $^1$H NMR chart. Note that FIG. 13B is an enlarged chart of FIG. 13A. The measurement results demonstrate that the objective substance 5,6-bis[4'-(10-phenyl-9-anthryl)biphenyl-4-yl]-2,2'-bipyridine (abbreviation: PAPP2BPy) was able to be obtained.

Figure 14A:
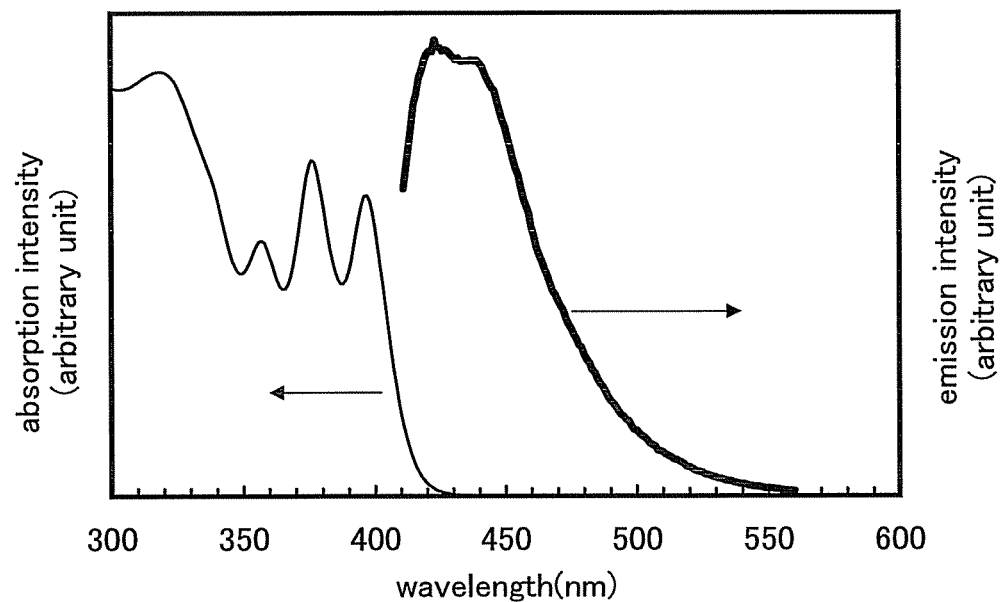
FIGS. 14A and 14B each show an absorption and emission spectra of PAPP2BPy.
Figure 14B:
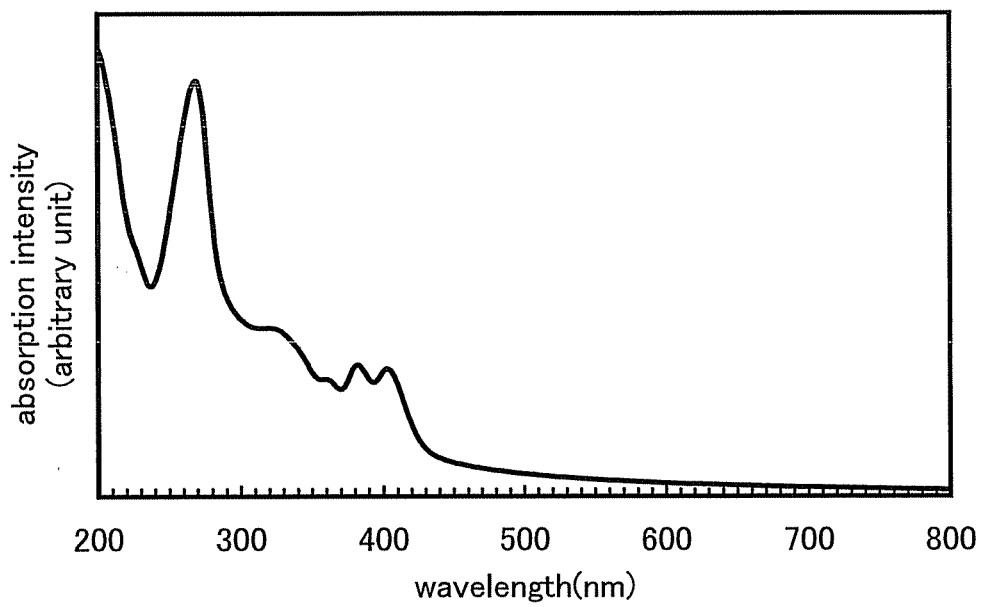

FIG. 14A shows an absorption spectrum and an emission spectrum of PAPP2BPy in a toluene solution of PAPP2BPy, and FIG. 14B shows an absorption spectrum of a thin film of PAPP2BPy. The absorption spectrum was measured using an ultraviolet-visible spectrophotometer (V-550, produced by JASCO Corporation). The measurements were performed with samples prepared in such a manner that the solution was put in a quartz cell and the thin film was obtained by evaporation onto a quartz substrate. The absorption spectrum of PAPP2BPy in the toluene solution of PAPP2BPy was obtained by subtracting the absorption spectra of quartz and toluene from the absorption spectra of quartz and the solution, and the absorption spectrum of the thin film was obtained by subtracting the absorption spectrum of the quartz substrate from the absorption spectra of the quartz substrate and the thin film. In FIGS. 14A and 14B, the horizontal axis indicates the wavelength (nm) and the vertical axis indicates the intensity (arbitrary unit). In the case of the toluene solution, absorption peaks were observed at around 397 nm, 376 nm, and 357 nm, and an emission wavelength peak was observed at 423 nm (at an excitation wavelength of 394 nm). In the case of the thin film, absorption peaks were observed at around 403 nm, 382 nm, 360 nm, 329 nm, and 269 nm.

A thermogravimetry-differential thermal analysis (TG-DTA) of the obtained PAPP2BPy was performed. The measurement was conducted by using a high vacuum differential type differential thermal balance (TG/DTA 2410SA, manufactured by Bruker AXS K.K.). The measurement was carried out under a nitrogen stream (a flow rate of 200 mL/min) at normal pressure at a temperature rising rate of 10° C./min. The relationship between weight and temperature (thermogravimetry) demonstrates that the 5% weight loss temperature was 500° C. or higher. Thus, PAPP2BPy was indicative of high heat resistance.

Furthermore, the ionization potential of PAPP2BPy in a thin film state was measured by a photoelectron spectrometer (AC-2, produced by Riken Keiki, Co., Ltd.) in the atmosphere. The obtained value of the ionization potential was converted into a negative value to give a HOMO level of PAPP2BPy of −5.87 eV. From the data of the absorption spectrum of the thin film in FIG. 14B, the absorption edge of PAPP2BPy, which was obtained from a Tauc plot with an assumption of direct transition, was 2.92 eV. Therefore, the optical energy gap of PAPP2BPy in a solid state can be estimated at 2.92 eV; from the values of the HOMO level obtained above and this energy gap, the LUMO level of PAPP2BPy can be estimated at −2.95 eV. This reveals that PAPP2BPy in the solid state has an energy gap as wide as 2.92 eV.

Electrochemical characteristics (oxidation and reduction characteristics) of a solution of PAPP2BPy were measured by cyclic voltammetry (CV). Note that an electrochemical analyzer (ALS model 600A or 600C, produced by BAS Inc.) was used for the measurements.

In the measurements, the potential of a working electrode with respect to the reference electrode was changed within an appropriate range, so that the oxidation peak potential and the reduction peak potential were each obtained. From the obtained peak potentials, the HOMO and LUMO levels of PAPP2BPy were respectively calculated at −5.79 eV and −2.73 eV.

The CV measurements and calculation for the HOMO level and the LUMO level were conducted in the same manner as that in Example 1.

In the measurement of the oxidation characteristics, one cycle was scanning in which the potential of the working electrode with respect to the reference electrode was changed from −0.25 V to 1.10 V and then changed from 1.10 V to −0.25 V.

In the measurements of the reduction characteristics, one cycle was scanning in which the potential of the working electrode with respect to the reference electrode was changed from −1.16 V to −2.60 V and then changed from −2.60 V to −1.16 V.

The oxidation peak potential $E_{pa}$ was 0.92 V and the reduction peak potential $E_{pc}$ was 0.77 V according to the measurement of the oxidation characteristics of PAPP2BPy. The half-wave potential $E_{1/2}$ was therefore 0.85 V, and since the potential energy of the reference electrode, which was used in the measurements, with respect to the vacuum level is −4.94 eV, the HOMO level of the solution of PAPP2BPy can be calculated as follows: −4.94−0.85=−5.79 eV.

The reduction peak potential $E_{pc}$ was −2.24 V and the oxidation peak potential $E_{pa}$ was −2.19 V according to the measurement of the reduction characteristics of PAPP2BPy. The half-wave potential $E_{1/2}$ was therefore −2.22 V, and since the potential energy of the reference electrode, which was used in the measurements, with respect to the vacuum level is −4.94 eV, the LUMO level of the solution of PAPP2BPy can be calculated as follows: −4.94−(−2.22)=−2.73 eV.

Example 3

In this example, a light-emitting element of one embodiment of the present invention will be described with reference to FIG. 1A. Chemical formulae of materials used in this example are shown below. The light-emitting element of this example is a light-emitting element in which a blue fluorescent material is used as an emission center material and the bipyridine compound described in Embodiment 1 is used for an electron-transport layer.

(i)

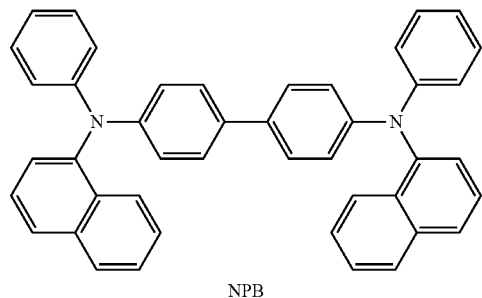

NPB (ii)

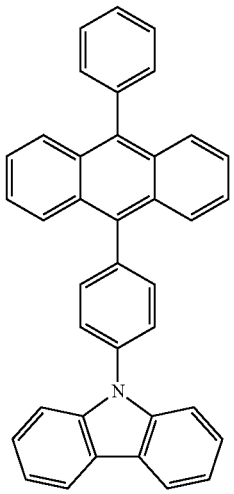

CzPA

-continued (iii)

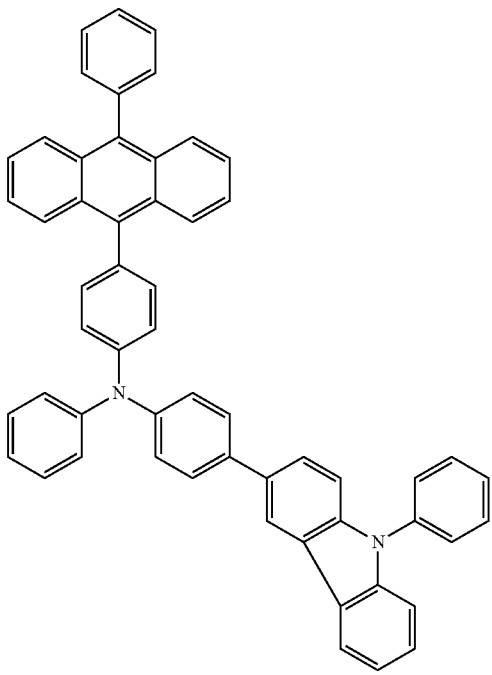

PCBAPA (100)

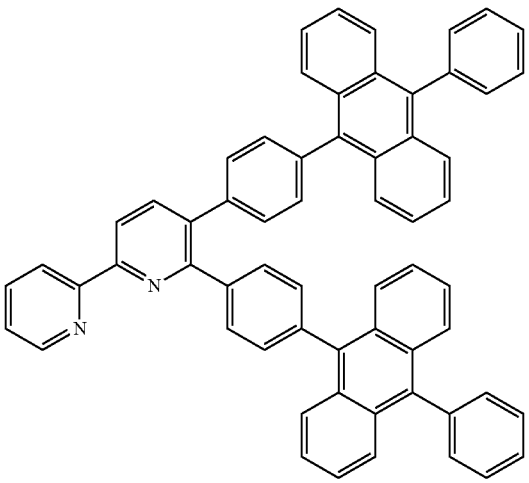

PAP2BPy (iv)

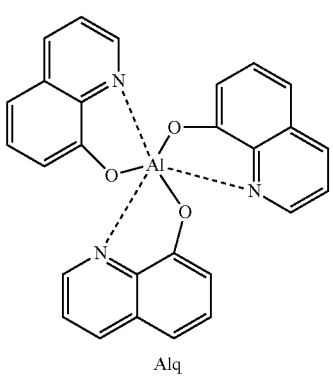

Alq

A method for manufacturing Light-emitting Element 1 of this example will be described below.

(Manufacturing Method of Light-emitting Element 1 and Comparative Light-emitting Element 1)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 is an electrode that functions as an anode of a light-emitting element.

Next, in pretreatment for forming the light-emitting element over the substrate, a surface of the substrate was washed with water and baked at 200° C. for one hour, and then UV ozone treatment was performed for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was allowed to cool for about 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to about $10^{-4}$ Pa. After that, over the first electrode 101, 4,4'-bis[N-(1-naphthyl)-N-phenylamino]biphenyl (abbreviation: NPB) represented by Structural Formula (i) and molybdenum(VI) oxide were co-evaporated by an evaporation method using resistance heating, so that the hole-injection layer 111 was formed. The thickness of the hole-injection layer 111 was set to 50 nm, and the weight ratio of NPB to molybdenum oxide was adjusted to 4:1 (=NPB:molybdenum oxide). Note that the co-evaporation method refers to an evaporation method in which evaporation is carried out from a plurality of evaporation sources at the same time in one treatment chamber.

Next, a film of NPB was formed to a thickness of 10 nm over the hole-injection layer 111 to form the hole-transport layer 112.

Furthermore, 9-[4-(N-carbazolyl)]phenyl-10-phenylanthracene (abbreviation: CzPA) represented by Structural Formula (II) and 4-(10-phenyl-9-anthryl)-4'-(9-phenyl-9H-carbazol-3-yl)triphenylamine (abbreviation: PCBAPA) represented by Structural Formula (iii) were co-evaporated over the hole-transport layer 112, thereby forming the light-emitting layer 113. The weight ratio of CzPA to PCBAPA was adjusted to 1:0.1 (=CzPA:PCBAPA). The thickness of the light-emitting layer 113 was set to 30 nm.

Furthermore, 5,6-bis[4-(10-phenyl-9-anthryl)phenyl]-2,2'-bipyridine (abbreviation: PAP2BPy), which is described as Structural Formula (100) in Embodiment 1, was formed to a thickness of 30 nm over the light-emitting layer 113, whereby forming the electron-transport layer 114.

Then, a film of lithium fluoride (LiF) was formed to a thickness of 1 mm over the electron-transport layer 114 to form the electron-injection layer 115.

Lastly, an aluminum film was formed by evaporation to a thickness of 200 nm as the second electrode 102 functioning as a cathode. Thus, Light-emitting Element 1 of this example was fabricated.

The Comparative Light-emitting Element 1 was manufactured in such a manner that instead of PAP2BPy, tris(8-quinolinolato)aluminum(III) (abbreviation: Alq) represented by Structural Formula (iv) was used as a material for the electron-transport layer 114 in Light-emitting Element 1.

Note that in all the above evaporation steps, evaporation was performed by a resistance-heating method.

Element structures of Light-emitting Element 1 and Comparative Light-emitting Element 1 obtained as described above are shown in Table 1.

TABLE 1

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITSO 110 nm | NPB:MoOx (=4:1) 50 nm | NPB 10 nm | CzPA: PCBAPA (=1:0.1) 30 nm | PAP2BPy 30 nm | LiF 1 nm | Al 200 nm |
| Comparative Light-emitting Element 1 | | | | | Alq 30 nm | | |

In a glove box containing a nitrogen atmosphere, Light-emitting Element 1 and Comparative Light-emitting Element 1 were each sealed with a glass substrate so as not to be exposed to the air (specifically, a sealant was applied onto an outer edge of the element and heat treatment was performed at 80° C. for an hour at the time of sealing). Then, operation characteristics of the light-emitting elements were measured. Note that the measurement was carried out at room temperature (in an atmosphere kept at 25° C.).

Figure 15:
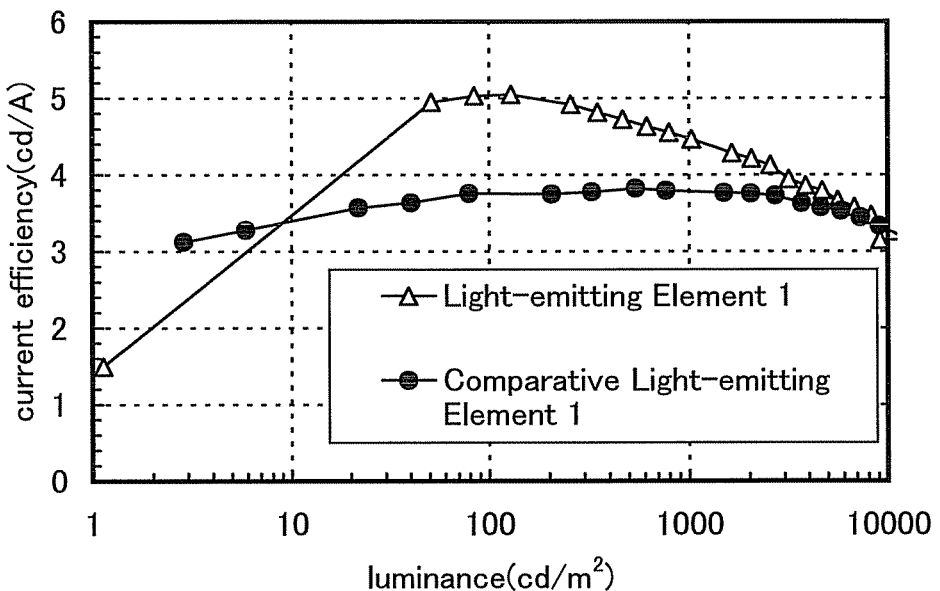
FIG. 15 shows current efficiency versus luminance characteristics of Light-emitting Element 1 and Comparative Light-emitting Element 1.
Figure 16:
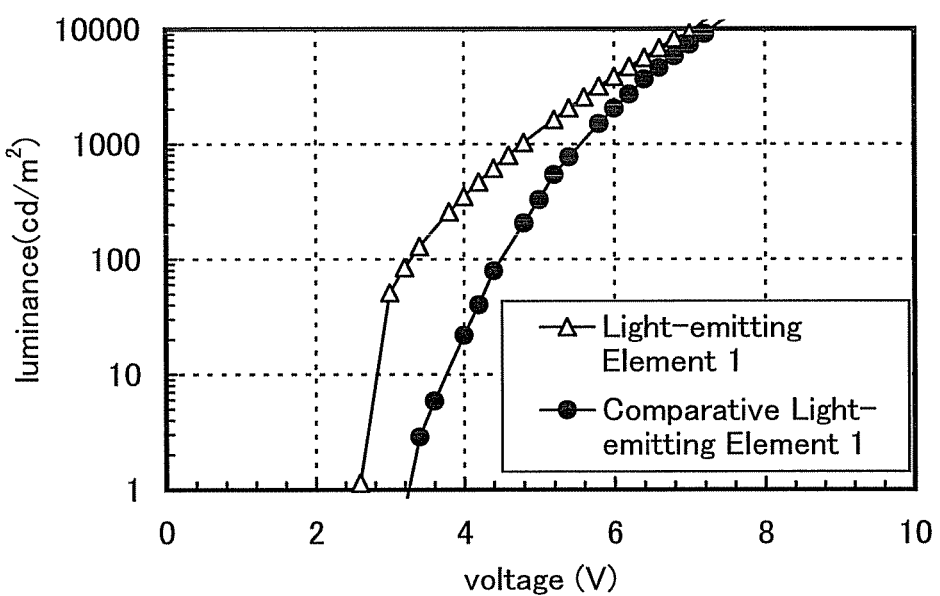
FIG. 16 shows luminance versus voltage characteristics of Light-emitting Element 1 and Comparative Light-emitting Element 1.
Figure 17:
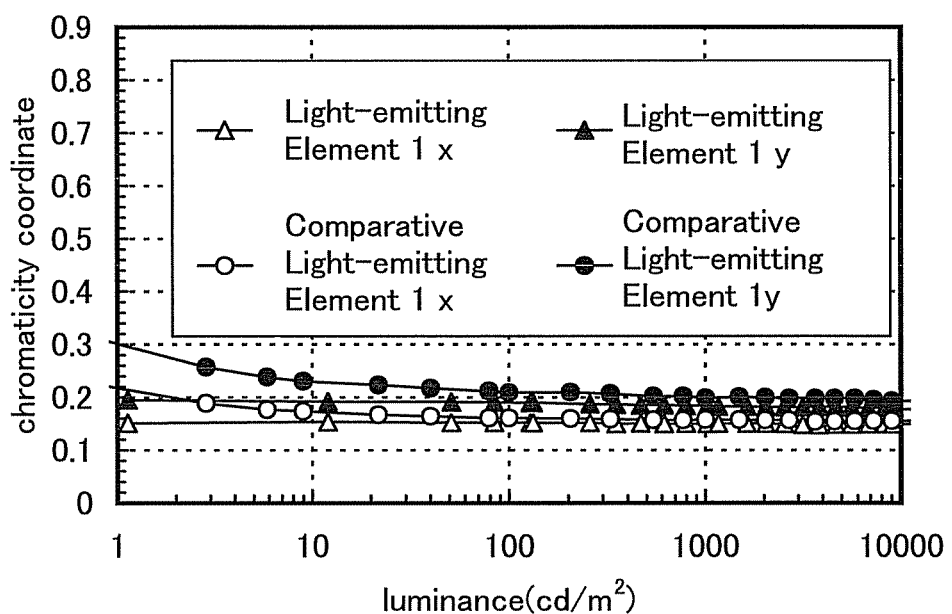
FIG. 17 shows chromaticity versus luminance characteristics of Light-emitting Element 1 and Comparative Light-emitting Element 1.

FIG. 15 shows current efficiency-luminance characteristics of Light-emitting Element 1 and Comparative Light-emitting Element 1. In FIG. 15, the horizontal axis indicates luminance (cd/m$^2$) and the vertical axis indicates current efficiency (cd/A). FIG. 16 shows luminance-voltage characteristics of Light-emitting Element 1 and Comparative Light-emitting Element 1. In FIG. 16, the horizontal axis indicates voltage (V) and the vertical axis indicates luminance (cd/m$^2$). FIG. 17 shows chromaticity coordinate-luminance characteristics of Light-emitting Element 1 and Comparative Light-emitting Element 1. In FIG. 17, the horizontal axis indicates luminance (cd/m$^2$) and the vertical axis indicates chromaticity coordinate (the x-coordinate or the y-coordinate). Table 2 shows voltage (V), current density (mA/cm$^2$), CIE chromaticity coordinates (x, y), current efficiency (cd/A), and external quantum efficiency (%) of each light-emitting element at a luminance of around 1000 cd/m$^2$.

TABLE 2

| | Voltage (V) | Current Density (mA/cm$^2$) | Chromaticity x | Chromaticity y | Current Efficiency (cd/A) | External Quantum Efficiency (%) |
|---|---|---|---|---|---|---|
| Light-emitting Element 1 | 4.8 | 23.0 | 0.15 | 0.18 | 4.5 | 3.2 |
| Comparative Light-emitting Element 1 | 5.4 | 20.3 | 0.16 | 0.20 | 3.8 | 2.5 |

*Xround off the values to one decimal place.

Figure 18:
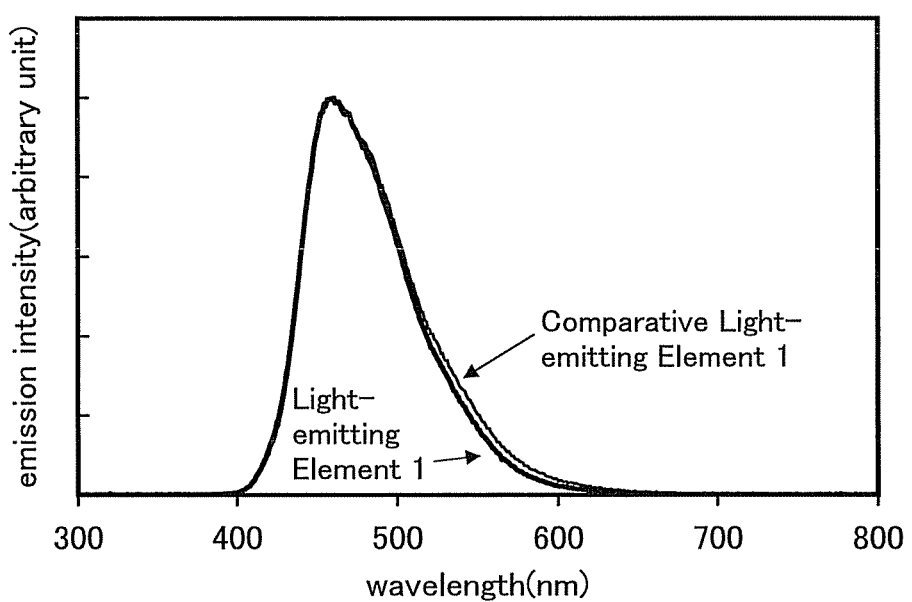
FIG. 18 shows emission spectra of Light-emitting Element 1 and Comparative Light-emitting Element 1.

FIG. 18 shows emission spectra of Light-emitting Element 1 and Comparative Light-emitting Element 1 which were obtained when a current of 0.1 mA was made to flow in Light-emitting Element 1 and Comparative Light-emitting Element 1. In FIG. 18, the horizontal axis indicates wavelength (nm) and the vertical axis indicates emission intensity (arbitrary unit).

As shown in FIG. 17 and Table 2, the CIE chromaticity coordinates of Light-emitting Element 1 were (x, y)=(0.15, 0.18) at a luminance of around 1000 cd/m². It was found that Light-emitting Element 1 exhibited light emission emanating from PCBAPA.

FIG. 16 and Table 2 show that Light-emitting Element 1 is a light-emitting element driven at a lower voltage than a light-emitting element using Alq that is widely used. In Light-emitting Element 1, PAP2BPy that is the bipyridine compound of one embodiment of the present invention was used as a material for an electron-transport layer. Accordingly, a light-emitting element which is driven at low voltage can be achieved.

As shown in FIG. 17, Light-emitting Element 1 shows substantially no change in color over a range from low luminance to high luminance. It can be said from this result that Light-emitting Element 1 is an element having excellent carrier balance.

As described above, a light-emitting element can be manufactured with the use of PAP2BPy manufactured in Example 1 as a material for an electron-transport layer. Furthermore, the light-emitting element can be driven at a low voltage and have a high emission efficiency.

This application is based on Japanese Patent Application serial no. 2012-032720 filed with Japan Patent Office on Feb. 17, 2012, the entire contents of which are hereby incorporated by reference.

What is claimed is:

1. A compound represented by a formula (G1),

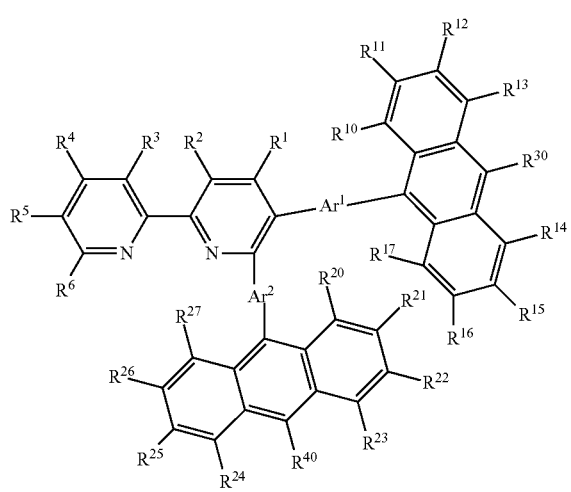

(G1)

wherein $R^1$ to $R^6$, $R^{10}$ to $R^{17}$, and $R^{20}$ to $R^{27}$ each independently represent hydrogen or an alkyl group having 1 to 4 carbon atoms, wherein $Ar^1$ and $Ar^2$ each independently represent an arylene group having 6 to 13 carbon atoms, and wherein $R^{30}$ and $R^{40}$ each independently represent any of hydrogen, an alkyl group having 1 to 4 carbon atoms, and an aryl group having 6 to 13 carbon atoms.

2. The compound according to claim 1, wherein $R^1$ to $R^6$ represent hydrogen.

3. The compound according to claim 1, wherein $R^1$ to $R^6$, $R^{10}$ to $R^{17}$, and $R^{20}$ to $R^{27}$ represent hydrogen.

4. The compound according to claim 1, wherein $R^{30}$ and $R^{40}$ each independently represent the aryl group having 6 to 13 carbon atoms.

5. The compound according to claim 1, wherein $R^{30}$ and $R^{40}$ each independently represent a phenyl group or a biphenyl group.

6. The compound according to claim 1, wherein $Ar^1$ and $Ar^2$ each independently represent a phenylene group or a biphenyldiyl group.

7. The compound according to claim 1, wherein the compound is represented by a formula (100)

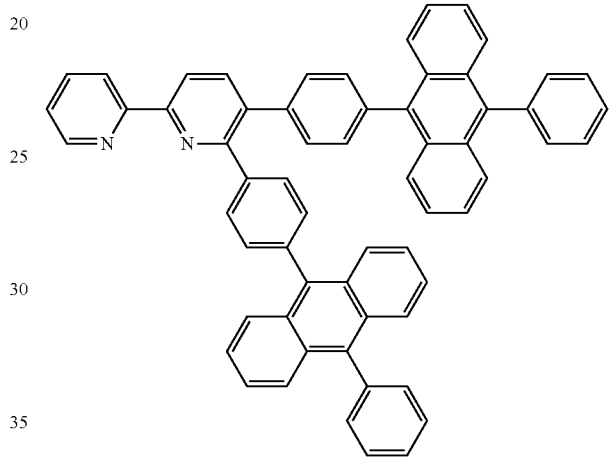

(100)

8. The compound according to claim 1, wherein the compound is represented by a formula (106)

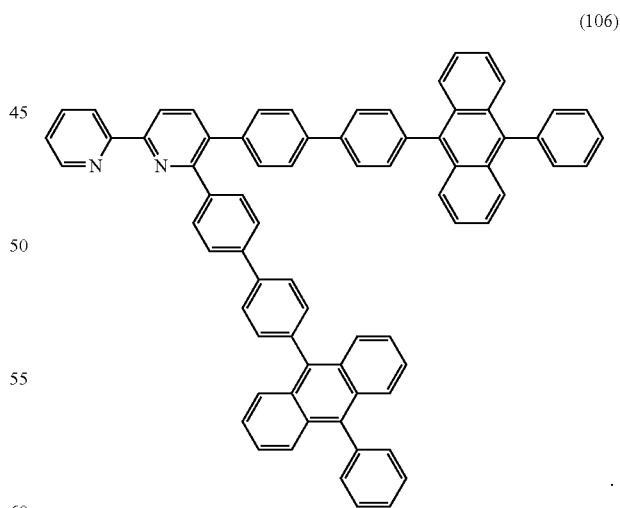

(106)

9. A transistor comprising;
a source electrode and a drain electrode;
an active layer comprising the compound according to claim 1 between the source electrode and the drain electrode; and
a gate electrode in the active layer.

10. A light-emitting element comprising;
a first electrode;
a second electrode; and
a layer comprising an organic compound between the first electrode and the second electrode,
wherein the organic compound comprises a compound represented by a formula (G1),

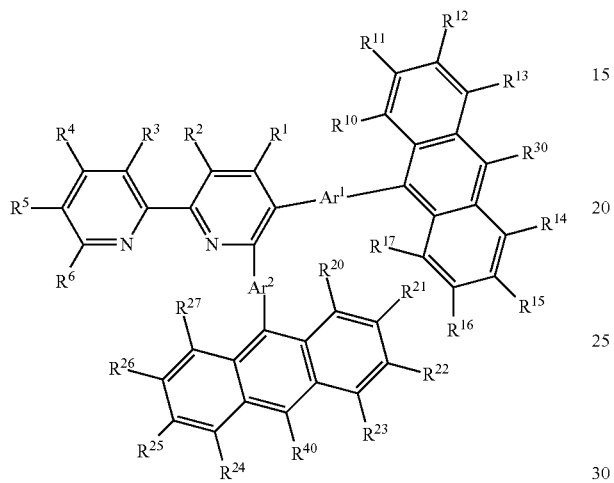

(G1)

wherein $R^1$ to $R^6$, $R^{10}$ to $R^{17}$, and $R^{20}$ to $R^{27}$ each independently represent hydrogen or an alkyl group having 1 to 4 carbon atoms, wherein $Ar^1$ and $Ar^2$ each independently represent an arylene group having 6 to 13 carbon atoms, and wherein $R^{30}$ and $R^{40}$ each independently represent any of hydrogen, an alkyl group having 1 to 4 carbon atoms, and an aryl group having 6 to 13 carbon atoms.

11. The light-emitting element according to claim 10, wherein $R^1$ to $R^6$ represent hydrogen.

12. The light-emitting element according to claim 10, wherein $R^1$ to $R^6$, $R^{10}$ to $R^{17}$, and $R^{20}$ to $R^{27}$ represent hydrogen.

13. The light-emitting element according to claim 10, wherein $R^{30}$ and $R^{40}$ each independently represent the aryl group having 6 to 13 carbon atoms.

14. The light-emitting element according to claim 10, wherein $R^{30}$ and $R^{40}$ each independently represent a phenyl group or a biphenyl group.

15. The light-emitting element according to claim 10, wherein $Ar^1$ and $Ar^2$ each independently represent a phenylene group or a biphenyldiyl group.

16. The light-emitting element according to claim 10, wherein the compound is represented by a formula (100)

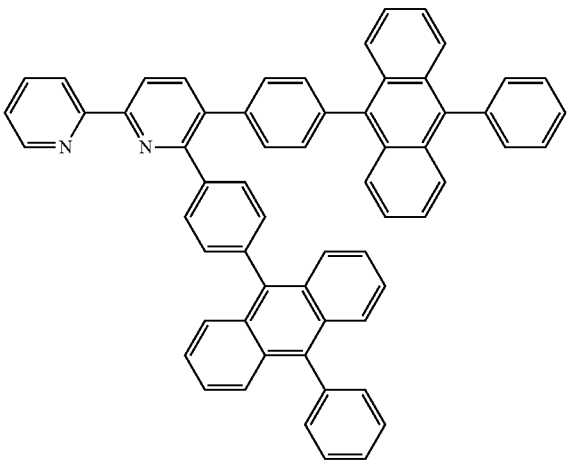

(100)

17. The light-emitting element according to claim 10, wherein the compound is represented by a formula (106)

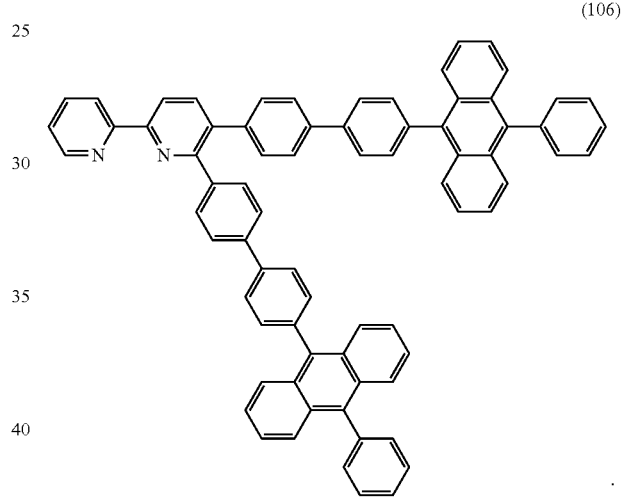

(106)

18. A lighting module comprising the light-emitting element according to claim 10.

19. A light-emitting device comprising:
the light-emitting element according to claim 10, and
a unit for controlling the light-emitting element.

20. A display device comprising:
the light-emitting element according to claim 10 in a display portion, and
a unit for controlling the light-emitting element.

21. A lighting device comprising:
the light-emitting element according to claim 10 in a lighting portion, and
a unit for controlling the light-emitting element.

22. An electronic device comprising the light-emitting element according to claim 10.

* * * * *